(12) United States Patent  
Schultz et al.

(10) Patent No.: US 8,507,469 B2  
(45) Date of Patent: Aug. 13, 2013

(54) AZETIDIN COMPOUNDS SUITABLE FOR TREATING DISORDERS THAT RESPOND TO MODULATION OF THE SEROTONIN 5-HT$_6$ RECEPTOR

(75) Inventors: Thomas Schultz, Ludwigshafen (DE); Wilfried Braje, Ludwigshafen (DE); Sean Colm Turner, Ludwigshafen (DE); Andreas Haupt, Ludwigshafen (DE); Udo Lange, Ludwigshafen (DE); Karla Drescher, Ludwigshafen (DE); Karsten Wicke, Ludwigshafen (DE); Liliane Unger, Ludwigshafen (DE); Mario Mezler, Ludwigshafen (DE); Matthias Mayrer, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 274 days.

(21) Appl. No.: 12/532,406

(22) PCT Filed: Mar. 20, 2008

(86) PCT No.: PCT/EP2008/053389  
§ 371 (c)(1),  
(2), (4) Date: Feb. 2, 2010

(87) PCT Pub. No.: WO2008/116833  
PCT Pub. Date: Oct. 2, 2008

(65) Prior Publication Data  
US 2010/0137280 A1     Jun. 3, 2010

(30) Foreign Application Priority Data  
Mar. 23, 2007  (EP) .................... 07104805

(51) Int. Cl.  
*A61K 31/397*  (2006.01)  
*C07D 403/04*  (2006.01)  
*C07D 471/04*  (2006.01)

(52) U.S. Cl.  
USPC ...... 514/210.21; 544/236; 546/113; 546/118; 546/119; 548/259; 548/306.1; 548/361.1; 548/466

(58) Field of Classification Search  
USPC ........... 548/306.1, 361.1, 259, 466; 546/113, 546/118, 119; 544/236  
See application file for complete search history.

(56) References Cited

FOREIGN PATENT DOCUMENTS

| WO | 98/27081 A1 | 6/1998 |
|---|---|---|
| WO | 00/05225 A1 | 2/2000 |
| WO | 00/63203 A1 | 10/2000 |
| WO | 01/05758 A2 | 1/2001 |
| WO | 03/104193 A1 | 12/2003 |
| WO | 2005/026125 A1 | 3/2005 |
| WO | 2005/037834 A1 | 4/2005 |
| WO | 2006/062481 A1 | 6/2006 |
| WO | 2006/081332 A1 | 8/2006 |
| WO | 2007/004959 A1 | 1/2007 |
| WO | 2007/006677 A1 | 1/2007 |

OTHER PUBLICATIONS

Parkinson's disease [online] retrieved on Jan. 26, 2011 from the internet. URL; http://www.mayoclinic.com/health/parkinsons-disease/DS00295.*

(Continued)

*Primary Examiner* — Shawquia Young  
(74) *Attorney, Agent, or Firm* — Lisa V. Mueller; Michael Best & Friedrich LLP

(57) ABSTRACT

The present invention relates to compounds of formula (I)

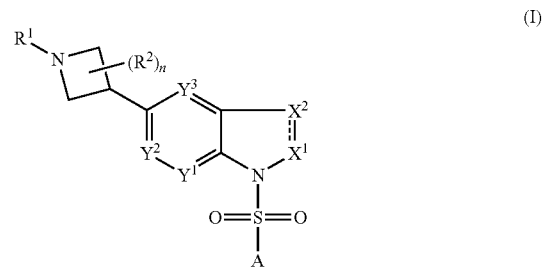

(I)

wherein A is $C_1$-$C_6$-alkyl, $C_1$-$C_6$-haloalkyl, $C_1$-$C_6$-hydroxyalkyl, $C_2$-$C_6$-alkenyl, $C_2$-$C_6$-halo-alkenyl, $C_3$-$C_6$-cycloalkyl, aryl-$C_1$-$C_4$-alkyl, aryl-$C_2$-$C_4$-alkenyl, aryl or hetaryl; ----- is a single or double bond; $X^1$ and $X^2$ are N, $CR^{x1}$, $NR^{x2}$ or $CR^{x3}R^{x4}$; $R^{x1}$, $R^{x3}$ and $R^{x4}$ are H, halogen, CN, $NO_2$, $C_1$-$C_6$-alkyl, $C_1$-$C_6$-alkoxy, $C_1$-$C_6$-alkylcarbonyl, etc. or two geminal radicals $R^{x3}$ and $R^{x4}$ together with the carbon atom to which they are bound may form a carbonyl group or a 3- to 6-membered carbocyclic or heterocyclic spiro-annulated ring; $R^{x2}$ is hydrogen, $C_1$-$C_6$-alkyl, $C_1$-$C_6$-alkylcarbonyl, $C_1$-$C_6$-haloalkyl, etc.; or two vicinal radicals $R^{x1}$, $R^{x2}$, $R^{x3}$ or $R^{x4}$ together with $X^1$ and $X^2$ form a five- or six-membered carbocyclic or heterocyclic fused ring; $Y^1$, $Y^2$ and $Y^3$ are N or $CR^y$; $R^y$ is H, halogen, CN, $NO_2$, $C_1$-$C_6$-alkyl, $C_1$-$C_6$-alkoxy, $C_1$-$C_6$-alkylcarbonyl, $C_1$-$C_6$-haloalkyl, etc.; wherein a maximum of 3 of the radicals $X^1$, $X^2$, $Y^1$, $Y^2$ and $Y^3$ are selected from $NR^{x1}$ and N; $R^1$ is hydrogen, $C_1$-$C_6$-alkyl, $C_1$-$C_6$-hydroxyalkyl, $C_1$-$C_6$-haloalkyl, etc.; $R^2$ is $C_1$-$C_4$-alkyl or $C_1$-$C_4$-haloalkyl; n is 0, 1 or 2; physiologically tolerated acid addition salts and the N-oxides thereof, pharmaceutical composition comprising them, a method for treating medical disorders selected from diseases of the central nervous system, addiction diseases or obesity, said method comprising administering an effective amount of such compounds to a subject in need and the use of such a compound for preparing a pharmaceutical compositions.

44 Claims, No Drawings

(56) References Cited

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Ballaz et al. (Neuroscience, 2007, 147:428-438).
Holenz, J., et al., "Medicinal chemistry strategies to 5-HT6 receptor ligands as potential cognitive enhancers and antiobesity agents," Drug Discovery Today, vol. 11, Nos. 7-8, Apr. 2006, pp. 283-299.
Heal, D.J., et al., "Selective 5-HT6 receptor ligands: progress in the development of a novel pharmacological approach to the treatment of obesity and related metabolic disorders," Pharmacology and Therapeutics, vol. 117, No. 2, Oct. 30, 2007, pp. 207-231.
International Search Report from International Application Publication No. WO 2008/116833 A1.
Written Opinion from International Application Publication No. WO 2008/116833 A1.

* cited by examiner

AZETIDIN COMPOUNDS SUITABLE FOR TREATING DISORDERS THAT RESPOND TO MODULATION OF THE SEROTONIN 5-HT$_6$ RECEPTOR

RELATED APPLICATION INFORMATION

This application is filed under 35 USC §371 from and claims priority to PCT Patent Application No. PCT/EP2008/053389, which claims the priority benefit of European application serial number EP 07104805.2, filed on Mar. 23, 2007, the teachings and content of which are hereby incorporated by reference herein.

BACKGROUND OF THE INVENTION

The present invention relates to novel azetidin compounds. The compounds possess valuable therapeutic properties and are particularly suitable, for treating diseases that respond to modulation of the serotonin 5-HT$_6$ receptor.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Until now, seven types of 5-HT receptors have been identified: 5-HT$_1$ (with subtypes 5-HT$_{1A}$, 5-HT$_{1B}$, 5-HT$_{1D}$, 5-HT$_{1E}$ and 5-HT$_{1F}$), 5-HT$_2$ (with subtypes 5-HT$_{2A}$, 5-HT$_{2B}$ and 5-HT$_{2C}$), 5-HT$_3$, 5-HT$_4$, 5-HT$_5$ (with subtypes 5-HT$_{5A}$ and 5-HT$_{5B}$), 5-HT$_6$ and 5-HT$_7$. Most of these receptors are coupled to G-proteins that affect the activities of either adenylate cyclase or phospholipase Cγ.

The human 5-HT$_6$ receptors are positively coupled to adenylyl cyclase. They are distributed throughout the limbic, striatal and cortical regions of the brain and show a high affinity to antipsychotics.

The modulation of the 5-HT$_6$ receptor by suitable substances is expected to improve certain disorders including cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

Compounds having an affinity for the 5-HT$_6$ receptor have been described in the prior art, e.g. in WO 2007/006677, WO 2007/004959, WO 2006/081332, WO 2006/062481, WO 2005/037834, WO 2005/026125, WO 00/05225 and WO 98/27081.

WO 01/05758 discloses compounds of the following formula,

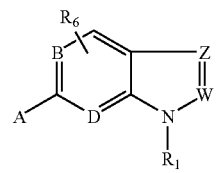

wherein B, D and W are nitrogen or CH, Z is nitrogen or a substituted carbon atom, A is a radical containing an amino moiety or a mono- or bicyclic heterocyclic moiety, R$_1$ may inter alia be an arylsulfonyl group and R$_6$ is selected from H, alkyl, aryl, halogen, hydroxy, alkoxy, amino, alkylamino and dialkylamino. Those compounds are used for the treatment of migraine related to the 5-HT$_{1D}$ receptor.

WO 2005/037834 discloses compounds of the following formula,

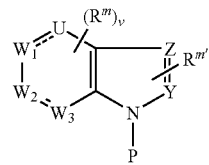

wherein ----- represents a single or double bond, P may inter alia be a substituted sulfonyl group, U is C or CH substituted by a group containing a nitrogen-containing moiety, which may be a heterocycle, W$_1$, W$_2$, W$_3$, Y and Z are each a carbon or one of said variables is a nitrogen atom and R$^m$ and R$^{m'}$ are selected from the group consisting of hydrogen, halogen, C$_1$-C$_6$-alkyl, hydroxy, C$_1$-C$_6$-alkoxy, C$_2$-C$_6$-alkenyl, phenyl, phenoxy, benzyloxy, benzoyl, —OCF$_3$, —CN, C$_1$-C$_6$-hydroxyalkyl, C$_1$-C$_6$-haloalkyl, —NR$_2$, —NO$_2$, —CONR$_2$, —NHSO$_2$R, —NRCOR', —SO$_2$NRR', —C(=O)R, C$_1$-C$_6$-alkoxycarbonyl, —S(O)$_e$R, —SCF$_3$, —CHF=CH$_2$, —OCF$_2$H and ethynyl. The compounds are mentioned to be useful for the treatment of 5-HT$_6$ receptor-related disorders.

However, there is still an ongoing need for providing compounds having high affinity for the 5-HT$_6$ receptor and which show high selectivity to this receptor. In particular the compounds should have low affinity to adrenergic receptors, such as $_1$-adrenergic receptor, histamine receptors, such as H$_1$-receptor, and dopaminergic receptors, such as D$_2$-receptor, in order to avoid or reduce considerable side effects associated with modulation of these receptors, such as postural hypotension, reflex tachycardia, potentiation of the antihypertensive effect of prazosin, terazosin, doxazosin and labetalol or dizziness associated to the blockade of the $_1$-adrenergic receptor, weight gain, sedation, drowsiness or potentiation of central depressant drugs associated to the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstruyl changes, sexual dysfunction in males), associated to the blockade of the D$_2$-receptor.

It is an object of the present invention to provide compounds which have a high affinity and selectivity for the $5$-$HT_6$ receptor, thus allowing the treatment of disorders related to or affected by the $5$-$HT_6$ receptor.

The compounds should also have good pharmacological profile, e.g. a good brain plasma ratio, a good bioavailability, good metabolic stability, or a decreased inhibition of the mitochondrial respiration.

SUMMARY OF THE INVENTION

It has now been found that the compounds of the formula (I) as defined herein, their physiologically tolerated acid addition salts and the N-oxides thereof exhibit to a surprising and unexpected degree, selective binding to the $5$-$HT_6$ receptor. Therefore, the present invention relates to the compounds of formula (I)

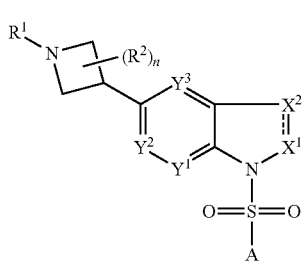

wherein
A is $C_1$-$C_6$-alkyl, $C_1$-$C_6$-haloalkyl, $C_1$-$C_6$-hydroxyalkyl, $C_2$-$C_6$-alkenyl, $C_2$-$C_6$-haloalkenyl, $C_3$-$C_6$-cycloalkyl, aryl-$C_1$-$C_4$-alkyl, aryl-$C_2$-$C_4$-alkenyl, aryl or hetaryl wherein cycloalkyl and the aryl or hetaryl moieties in the 5 last mentioned radicals may be unsubstituted or may carry 1, 2 or 3 substituents $R^a$, wherein
  $R^a$ is selected from the group consisting of halogen, CN, $NO_2$, $C_1$-$C_6$-alkyl, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_6$-alkoxy, $C_1$-$C_6$-hydroxyalkoxy, $C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkylcarbonyl, $C_1$-$C_6$-alkylcarbonylamino, $C_1$-$C_6$-haloalkyl-carbonylamino, carboxy, NH—C(O)—$NR^3R^4$, $NR^3R^4$, $NR^3R^4$—$C_1$-$C_6$-alkylene, O—$NR^3R^4$, wherein $R^3$ and $R^4$ in the last 4 mentioned radicals are independently of each other hydrogen, $C_1$-$C_6$-alkyl, $C_1$-$C_6$-haloalkyl, $C_1$-$C_6$-alkoxy or together with the nitrogen atom form an N-bound 5- to 7-membered saturated heterocycle, which may contain a further heteroatom selected from O, S and N as ring member, a saturated or unsaturated 3- to 7-membered heterocyclic ring, phenyl, benzyl, phenylsulfonyl, phenoxy and benzyloxy, wherein the 3- to 7-membered heterocyclic ring comprises as ring members 1, 2, 3 or 4 heteroatoms selected from N, O and S and may carry 1, 2 or 3 substituents selected from hydroxy, halogen, $C_1$-$C_6$-alkyl, $C_1$-$C_6$-haloalkyl and $C_1$-$C_6$-alkoxy and wherein the phenyl radical in phenyl, benzyl, phenylsulfonyl, phenoxy and benzyloxy is unsubstituted or may carry 1, 2 or 3 substituents selected from halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylcarbonyl, $C_1$-$C_6$-haloalkyl-carbonyl, $C_1$-$C_6$-alkylcarbonylamino, $C_1$-$C_6$-haloalkylcarbonylamino, carboxy, NH—C(O)—$NR^5R^6$, $NR^5R^6$, $NR^5R^6$—$C_1$-$C_6$-alkylene, O—$NR^5R^6$, wherein $R^5$ and $R^6$ are independently of each other hydrogen, $C_1$-$C_6$-alkyl, $C_1$-$C_6$-haloalkyl, $C_1$-$C_6$-alkoxy or together with the nitrogen atom form an N-bound 5- to 7-membered saturated heterocycle, which may contain a further heteroatom selected from O, S and N as ring member;
----- is a single bond or a double bond;
$X^1$ and $X^2$ are independently from each other N or $CR^{x1}$, if ----- is a double bond, or $NR^{x2}$ or $CR^{x3}R^{x4}$, if ----- is a single bond, wherein
  $R^{x1}$, $R^{x3}$ and $R^{x4}$ are independently from each other selected from hydrogen, halogen, CN, $NO_2$, $C_1$-$C_6$-alkyl, $C_1$-$C_6$-alkoxy, $C_1$-$C_6$-alkyl-carbonyl, $C_1$-$C_6$-haloalkyl, $C_1$-$C_6$-haloalkoxy, $C_1$-$C_6$-haloalkylcarbonyl, $C_1$-$C_6$-hydroxyalkyl, $C_3$-$C_6$-cycloalkyl, phenyl, phenoxy and benzyl-oxy, wherein the last four mentioned radicals may be unsubstituted or may carry 1, 2 or 3 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy,
  or two geminal radicals $R^{x3}$ and $R^{x4}$ together with the carbon atom to which they are bound may form a carbonyl group or a 3- or 6-membered carbocyclic or heterocyclic spiro-annulated ring, which may be unsubstituted or may carry 1, 2, 3, 4 or 5 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy, and
  $R^{x2}$ is hydrogen, $C_1$-$C_6$-alkyl, $C_1$-$C_6$-alkylcarbonyl, $C_1$-$C_6$-haloalkyl, $C_1$-$C_6$-haloalkylcarbonyl, $C_1$-$C_6$-hydroxyalkyl, $C_3$-$C_6$-cycloalkyl or phenyl, wherein the last two mentioned radicals may be unsubstituted or may carry 1, 2 or 3 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy,
  or two vicinal radicals selected from $R^{x1}$, $R^{x2}$, $R^{x3}$ and $R^{x4}$ together with $X^1$ and $X^2$ form a five- or six-membered carbocyclic or heterocyclic fused ring, which may be unsubstituted or may carry 1, 2, 3 or 4 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy;
$Y^1$, $Y^2$ and $Y^3$ are independently from each other N or $CR^y$, wherein
  $R^y$ is hydrogen, halogen, CN, $NO_2$, $C_1$-$C_6$-alkyl, $C_1$-$C_6$-alkoxy, $C_1$-$C_6$-alkylcarbonyl, $C_1$-$C_6$-haloalkyl, $C_1$-$C_6$-haloalkoxy, $C_1$-$C_6$-halo-alkylcarbonyl, $C_1$-$C_6$-hydroxyalkyl, $C_3$-$C_6$-cycloalkyl, phenyl, phenoxy or benzyloxy wherein the last four mentioned radicals may be unsubstituted or may carry 1, 2 or 3 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy;
wherein a maximum of 3, i.e. 0, 1, 2 or 3, in particular 0 or 1 of the moieties $X^1$, $X^2$, $Y^1$, $Y^2$ and $Y^3$ are $NR^x$ or N;
and wherein
$R^1$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, aryl-$C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl or $C_1$-$C_4$-alkoxycarbonyl;
$R^2$ is $C_1$-$C_4$-alkyl or $C_1$-$C_4$-haloalkyl;
n is 0, 1 or 2;

and to the physiologically tolerated acid addition salts and the N-oxides thereof.

The present invention also relates to a pharmaceutical composition which comprises at least one compound of the formula (I) and/or at least one physiologically tolerated acid addition salt of (I) and/or at least one N-oxide of (I), where appropriate together with physiologically acceptable carriers and/or auxiliary substances.

The present invention further relates to the use of a compound of the formula (I) and/or physiologically tolerated acid addition salts thereof and/or N-oxides of (I), for preparing a pharmaceutical composition, optionally together with at least one physiologically acceptable carrier or auxiliary substance.

The present invention further relates to the compounds of the formula (I) and physiologically tolerated acid addition salts thereof and the N-oxides of (I) for use as a medicament, in particular for use as a medicament for the treatment of a medical disorder or disease which responds to influencing by 5-$HT_6$ receptor ligands.

The present invention also relates to a method for treating disorders or diseases which respond to influencing by 5-$HT_6$ receptor ligands, said method comprising administering an effective amount of at least one compound of the formula (I) and/or at least one physiologically tolerated acid addition salt of (I) and/or at least one N-oxide of (I) to a subject in need thereof. Said diseases are for instance diseases/disorders of the central nervous system, addiction diseases or obesity.

DETAILED DESCRIPTION OF THE INVENTION

The diseases which respond to the influence of 5-$HT_6$ receptor ligands include, in particular, disorders and diseases of the central nervous system, in particular cognitive dysfunctions, such as a deficit in memory, cognition and learning, in particular associated with Alzheimer's disease, age-related cognitive decline and mild cognitive impairment, attention deficit disorder/hyperactivity syndrome (ADHD), personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

In this context a disease/disorder responding to influencing by 5-$HT_6$ receptor ligands is understood as a disease/disorder which is influenced by the modulation of the 5-$HT_6$ receptor function. Such a modulation is achieved by 5-$HT_6$ receptor ligands, i.e. compounds which bind to the 5-$HT_6$ receptor, thereby affecting the function of 5-$HT_6$ receptors.

According to the invention, at least one compound of the general formula (I) having the meanings mentioned at the outset is used for treating the above mentioned indications. Provided the compounds of the formula (I) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) and/or of their salts and/or their N-oxides.

It is likewise possible to use physiologically tolerated salts of the compounds of the formula (I), especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formula (I), if those compounds contain a basic nitrogen atom, such as the nitrogen atom of a pyridinyl substituent.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "$C_1$-$C_6$-alkyl" as used herein and in the alkyl moieties of $C_1$-$C_6$-haloalkyl, $C_1$-$C_6$-hydroxyalkyl, $C_1$-$C_6$-alkoxy, $C_1$-$C_6$-alkoxy-$C_1$-$C_4$-alkyl, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkylcarbonylamino, $C_3$-$C_6$-cycloalkyl-$C_1$-$C_4$-alkyl, aryl-$C_1$-$C_4$-alkyl or hetaryl-$C_1$-$C_4$-alkyl denotes in each case a straight-chain or branched alkyl group having from 1 to 6 carbon atoms, preferably 1 to 4 carbon atoms. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethyl-propyl, 1-ethyl-1-methylpropyl and 1-ethyl-2-methylpropyl.

The term "$C_1$-$C_6$-haloalkyl" as used herein and in the haloalkyl moieties of $C_1$-$C_6$-haloalkoxy, $C_1$-$C_6$-haloalkylthio, $C_1$-$C_6$-haloalkylsulfinyl, $C_1$-$C_6$-haloalkylsulfonyl, $C_1$-$C_6$-haloalkylcarbonyl, $C_1$-$C_6$-haloalkylcarbonylamino denotes in each case a straight-chain or branched alkyl group having from 1 to 6 carbon atoms, wherein the hydrogen atoms of this group are partially or totally replaced with halogen atoms. Preferred haloalkyl moieties are selected from $C_1$-$C_4$-haloalkyl, especially preferred from $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluorethyl, 2,2,2-trichloroethyl, pentafluoroethyl and the like.

The term "$C_1$-$C_6$-hydroxyalkyl" is a straight-chain or branched alkyl group having from 1 to 6, especially 1 to 4 carbon atoms (=$C_1$-$C_4$ hydroxyalkyl), in particular 1 to 3 carbon atoms (=$C_1$-$C_3$ hydroxyalkyl), wherein one of the hydrogen atoms is replaced by a hydroxy group, such as in 2-hydroxyethyl or 3-hydroxypropyl.

The term "$C_3$-$C_6$-cycloalkyl" as used herein and in the cycloalkyl moieties of $C_3$-$C_6$-cycloalkyl-$C_1$-$C_4$-alkyl and $C_3$-$C_6$-halocycloylkyl denotes in each case a cycloaliphatic radical having from 3 to 6 C atoms, such as cyclopropyl, cyclobutyl, cyclopentyl and cyclohexyl. The cycloalkyl radical may be unsubstituted or may carry 1, 2, 3 or 4 $C_1$-$C_4$-alkyl radicals, preferably a methyl radical. One alkyl radical is preferably located in the 1-position of the cycloalkyl radical, such as in 1-methylcyclopropyl or 1-methylcyclobutyl.

The term "$C_2$-$C_6$-alkenyl" as used herein and in the alkenyl moieties of $C_3$-$C_6$-haloalkenyl and aryl-$C_2$-$C_4$-alkenyl denotes in each case a singly unsaturated hydrocarbon radical having 2, 3, 4, 5 or 6 C-atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "aryl" as used herein denotes in each case a carbocyclic radical selected from the group consisting of phenyl and phenyl fused to a saturated or unsaturated 5- or 6-membered carbocyclic ring, such as naphthyl, 1,2-dihydronaphtyl, 1,2,3,4-tetrahydronaphtyl, indenyl or indanyl.

The term "hetaryl" as used herein denotes in each case a cyclic radical selected from the group consisting of monocyclic 5- or 6-membered heteroaromatic radicals comprising as ring members 1, 2 or 3 heteroatoms selected from N, O and S and a saturated or unsaturated 5- or 6-membered heterocyclic ring fused to a phenyl ring or to a 5- or 6-membered heteroaromatic radical, where the heterocyclic ring comprises as ring members 1, 2 or 3 heteroatoms selected from N, O and S.

Examples of 5- or 6-membered heteroaromatic radicals include 2-, 3-, or 4-pyridyl, 2-, 4- or 5-pyrimidinyl, pyrazinyl, 3- or 4-pyridazinyl, 2- or 3-thienyl, 2- or 3-furyl, 1-, 2- or 3-pyrrolyl, 2-, 3- or 5-oxazolyl, 3-, 4- or 5-isoxazolyl, 2-, 3- or 5-thiazolyl, 3-, 4- or 5-isothiazolyl, 1-, 3-, 4- or 5-pyrazolyl, 1-, 2-, 4- or 5-imidazolyl, 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, 2- or 5-(1,3,4-thiadiazol)yl, 4- or 5-(1,2,3-thiadiazol)yl, 3- or 5-(1,2,4-thiadiazol)yl 1H-, 2H- or 3H-1,2,3-triazol-4-yl, 2H-triazol-3-yl, 1H-, 2H-, or 4H-1,2,4-triazolyl and 1H- or 2H-tetrazolyl.

Examples of a saturated or unsaturated 5- or 6-membered heterocyclic ring fused to a phenyl ring include benzofuranyl, 2,3-dihydrobenzofuranyl, benzothienyl, indolyl, indazolyl, benzimidazolyl, benzoxathiazolyl, benzoxadiazolyl, benzothiadiazolyl, benzoxazinyl, dihydrobenzoxazinyl, chinolinyl, isochinolinyl, tetrahydroisochinolinyl, chromenyl, chromanyl, 2,3-dihydroindolyl, dihydroisoindolyl, benzomorpholinyl and the like, which may be unsubstituted or which may carry 1, 2 or 3 of the aforementioned radicals $R^a$. These fused hetaryl radicals may be bonded to the remainder of the molecule (more precisely to the sulfonyl group) via any ring atom of saturated or unsaturated 5- or 6-membered heterocyclic ring or via a carbon atom of the fused phenyl moiety.

Examples of a saturated or unsaturated 5- or 6-membered heterocyclic ring fused to a 5- or 6-membered heteroaromatic radical comprise inter alia purinyl, 1,8-naphtyridyl, pteridyl, pyrido[3,2-d]pyrimidyl, imidazo[2,1-b]thiazolyl, pyrido[3,2-b][1,4]oxazinyl, 3,4-dihydropyrido[3,2-b][1,4]oxazinyl or pyridoimidazolyl.

The term "saturated or unsaturated heterocyclic ring" in each case denotes a 3- to 7 membered cyclic radical containing at least one hetero atom selected from the group consisting of N, O and S. Examples for such saturated or unsaturated 3- to 7-membered heterocyclic rings comprise saturated or unsaturated, aromatic or non-aromatic heterocyclic rings. Examples therefore include, apart from the above-defined 5- or 6-membered heteroaromatic radicals, aziridyl, diaziridinyl, oxiranyl, azetidinyl, azetinyl, di- and tetrahydrofuranyl, pyrrolyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl and the like.

Examples for "N-bound 5- to 7-membered saturated heterocycle" are pyrrolidinyl, piperidinyl, piperazinyl, morpholinyl, imidazolidinyl, oxazolidinyl, thiazolidinyl or hexahydrodiazepinyl especially piperidinyl and morpholinyl.

With regard to their ability to bind to the 5-HT$_6$ receptor preference is given to compounds of formula (I), wherein the variables A, n, $R^1$, $R^2$, $X^1$, $X^2$, $Y^1$, $Y^2$ and $Y^3$ have the meanings given below.

The remarks made in the following with respect to preferred aspects of the invention, e.g. to preferred meanings of the variables of compound of the formula (I), to preferred compounds of the formula (I) and to preferred embodiments of the method or the use according to the invention, apply in each case on their own or to combinations thereof.

Preference is given to compounds of the formula (I), wherein A is mono- or bicyclic aryl or mono- or bicyclic hetaryl, wherein the cyclic radical A is unsubstituted or may carry 1, 2 or 3 substituents $R^a$, as defined above. Preferably A is selected from the group consisting of phenyl, naphthyl, thienyl, pyridyl, pyrimidyl, imidazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl, benzomorpholinyl, imidazo[2,1-b]thiazolyl, pyrido[3,2-b][1,4]oxazinyl, 3,4-dihydropyrido[3,2-b][1,4]oxazinyl or indanyl, in particular of the group consisting of phenyl, naphthyl, thienyl, pyridyl, pyrimidyl, imidazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl, benzomorpholinyl or indanyl, wherein the cyclic radical A is unsubstituted or may carry 1, 2 or 3 substituents $R^a$.

A preferred embodiment of the present application relates to compounds of the formula (I), wherein A is phenyl, which is unsubstituted or may carry 1, 2 or 3 substituents $R^a$.

Preference is given to compounds of the formula (I), wherein A is phenyl, which is unsubstituted or may carry 1, 2 or 3 substituents $R^a$, wherein the substituents $R^a$ are attached to the phenyl ring in ortho- and/or meta-position relative to the bonding-position. Very preferred are compounds of formula (I), wherein the substituent A is phenyl, which is substituted in the meta-position.

Preference is also given to compounds of the formula (I), wherein the radicals $R^a$ are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxY, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from halogen, CN, NO$_2$, $C_1$-$C_4$-alkyl, $C_1$-$C_4$-haloalkyl, $C_1$-$C_4$-alkoxy, $C_1$-$C_4$-haloalkoxy. More preference is given to radicals $R^a$ which are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

One of the substituents $R^a$ may also be saturated or unsaturated 3- to 7-membered heterocyclic ring comprising as ring members 1, 2, 3 or 4, preferably 1, 2 or 3 heteroatoms selected from N, O and S, examples including aziridyl, diaziridinyl, oxiranyl, azetidinyl, azetinyl, di- and tetrahydrofuranyl, pyrrolinyl, pyrrolidinyl, oxopyrrolidinyl, pyrazolinyl, pyrazolidinyl, imidazolinyl, imidazolidinyl, oxazolinyl, oxazolidinyl, oxo-oxazolidinyl, isoxazolinyl, isoxazolidinyl, piperidinyl, piperazinyl, morpholinyl, thiomorpholinyl, oxothiomorpholinyl, dioxothiomorpholinyl, preferably pyrrolinyl, morpholinyl, pyridyl and thiazolyl.

Examples for such preferred substituents A is selected from the group consisting of phenyl, 2-fluorophenyl, 3-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 2,3-dichlorophenyl, 3,4-dichlorophenyl, 3,5-dichlorophenyl, 2-tolyl, 3-tolyl, 2-isopropylphenyl, 3-isopropylphenyl, 2-difluoromethylphenyl, 3-difluoromethylphenyl, 2-trifluoromethylphenyl, 3-trifluoromethylphenyl, biphenyl-2-yl, biphenyl-3-yl, 2-methoxyphenyl, 3-methoxyphenyl, 2-difluoromethoxyphenyl, 3-difluoromethoxyphenyl, 2-trifluoromethoxyphenyl, 3-trifluoromethoxyphenyl, 2-phenoxyphenyl, 3-phenoxyphenyl, 4-(oxazol-5-yl)phenyl, 3-(pyrrolidin-1-yl)phenyl, 1-naphtyl, 2-naphtyl, pyridin-2-yl, pyridin-3-yl, pyridin-4-yl, 2-(pyrrolidin-1-yl)pyridin-4-yl, 6-morpholinylpyridin-3-yl, 6-phenoxypyridin-3-yl, thien-2-yl, 5-methylthien-2-yl, 5-(pyridin-2-yl)thien-2-yl, 5-(2-methylthiazol-4-yl)-thien-2-yl, 5-chloro-3-methyl-benzo[b]thien-2-yl, 2-methylthiazol-5-yl, 2,4-dimethyl-thiazol-5-yl, 4-methylthiazol-2-yl, 5-methylthiazol-2-yl, 3,5-dimethylisoxazol-4-yl, 1-methylimidazol-4-yl, benzothiazol-7-yl, 4-methylbenzomorpholin-8-yl, quinolin-8-yl, 5-methylpyridin-2-yl, 2-morpholin-4-ylpyridin-3-yl, 4-fluoro-3-(oxazol-4-yl)phenyl, quinolin-6-yl, 6-chloroimidazo[2,1-b]thiazol-5-yl, 4-methyl-3,4-dihydropyrido[3,2-b][1,4]oxazin-7-yl, isoquinolin-4-yl, 2,1,3-benzoxdiazol-4-yl.

Very preferred examples of substituents A are phenyl, 2-fluorophenyl, 3-fluorophenyl, 2,3-difluoro-phenyl, 3,4-difluorophenyl, 3,5-difluorophenyl, 2-chlororophenyl, 3-chlorophenyl, 2,3-dichloro-phenyl, 3,4-dichlorophenyl, 3,5-dichlorophenyl, 2-difluoromethylphenyl, 3-difluoromethylphenyl, 2-trifluoro-methylphenyl, 3-trifluoromethylphenyl, 2-difluoromethoxyphenyl, 3-difluoromethoxyphenyl, 2-trifluoromethoxyphenyl and 3-trifluoromethoxyphenyl.

Preference is also given to compounds of the formula (I) wherein the substituents $R^{x1}$, $R^{x3}$ and $R^{x4}$ are independently from each other selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy. More preferably $R^{x1}$, $R^{x3}$ and $R^{x4}$ are selected from hydrogen, halogen and CN. In particular $R^{x1}$ is hydrogen or halogen such as fluorine or chlorine and $R^{x3}$ and $R^{x4}$ are hydrogen. Most preferably $R^{x1}$, $R^{x3}$ and $R^{x4}$ are hydrogen.

The substituent $R^{x2}$ in compounds of the formula (I) preferably is hydrogen or $C_1$-$C_4$-alkyl.

The substituent $R^y$ in compounds of the formula (I) is preferably selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy. More preferably $R^y$ is hydrogen or halogen. Most preferably $R^y$ is hydrogen.

The radical $R^1$ in compounds of the formula (I) is preferably selected from the group consisting of hydrogen, $C_1$-$C_4$-alkyl, $C_1$-$C_4$-haloalkyl and $C_3$-$C_6$-cycloalkyl. More preferably the radical $R^1$ is hydrogen.

The radical $R^2$ in compounds of the formula (I) preferably is $C_1$-$C_4$-alkyl. More preferably $R^2$ is methyl.

The azetidin moiety of compounds (I), i.e. the moiety of the formula

wherein n and $R^2$ are as defined above and * indicates the bonding to $R^1$ or the aromatic ring, respectively is preferably selected from the moieties of formulae AZ.1, AZ.2, AZ.3, AZ.4 and AZ.5.

(AZ.1)

(AZ.2)

(AZ.3)

(AZ.4)

(AZ.5)

More preferably azetidin moiety is AZ.1. Thus, n preferably is 0.

According to a first embodiment of the present invention ----- in formula (I) is a single bond. In this embodiment the compounds of formula (I) are preferably selected from compounds of formulae I.A.1 to I.A.6

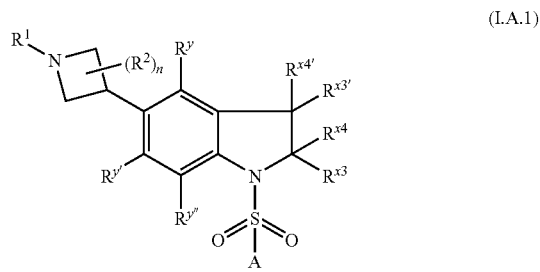
(I.A.1)

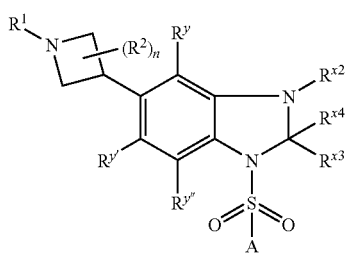 (I.A.2)

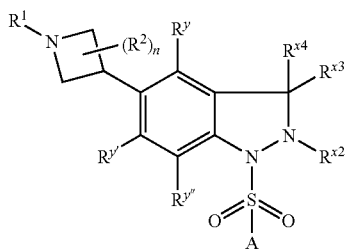 (I.A.3)

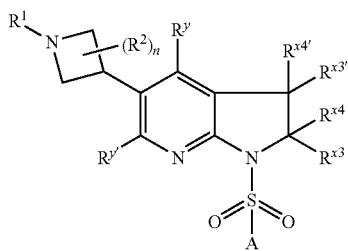 (I.A.4)

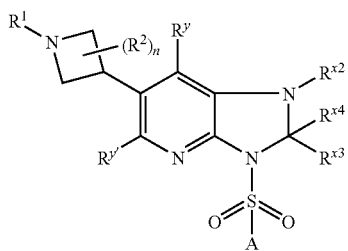 (I.A.5)

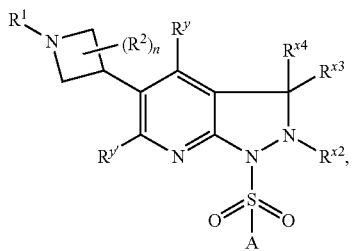 (I.A.6)

wherein the radicals A, $R^1$, $R^2$, n and $R^{x2}$ have one the meanings given before, $R^{x3}$ and $R^{x3'}$ independently from each other have one the meanings given for $R^{x3}$ before, $R^{x4}$ and $R^{x4'}$ independently from each other have one the meanings given for $R^{x4}$ before and $R^y$, $R^{y'}$ and $R^{y''}$ independently from each other have one the meanings given for $R^y$ before.

Particular preference is given to the compounds of formula I.A.1.

The radical $R^1$ in the compounds of the formulae I.A.1 to I.A.6 is preferably selected from the group consisting of hydrogen, $C_1$-$C_4$-alkyl, $C_1$-$C_4$-haloalkyl and $C_3$-$C_6$-cycloalkyl. More preferably the radical $R^1$ is hydrogen.

The radical $R^2$ in the compounds of the formulae I.A.1 to I.A.6 preferably is $C_1$-$C_4$-alkyl. More preferably $R^2$ is methyl.

The azetidin moiety in the compounds of the formulae I.A.1 to I.A.6 is preferably selected from the moieties of formulae AZ.1, AZ.2, AZ.3, AZ.4 and AZ.5.

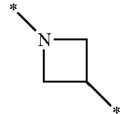 (AZ.1)

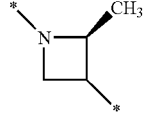 (AZ.2)

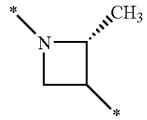 (AZ.3)

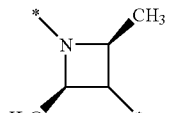 (AZ.4)

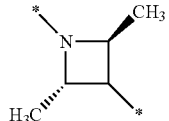 (AZ.5)

More preferably azetidin moiety is AZ.1. Thus, n preferably is 0.

A preferred embodiment of the present application relates to compounds of formulae I.A.1 to I.A.6, wherein A is phenyl, which is unsubstituted or may carry 1, 2 or 3 substituents $R^a$.

Preference is given to compounds of the formulae I.A.1 to I.A.6, wherein A is phenyl, which is unsubstituted or may carry 1, 2 or 3 substituents $R^a$, wherein the substituents $R^a$ are attached to the phenyl ring in ortho- and/or meta-position relative to the bonding-position. Very preferred are compounds of formulae I.A.1 to I.A.6, wherein the substituent A is phenyl, which is substituted in the meta-position.

Preference is also given to compounds of the formulae I.A.1 to I.A.6, wherein the radicals $R^a$ are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy. More preference is given to compounds of formulae I.A.1 to I.A.6, wherein the radicals $R^a$ are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

Preference is also given to compounds of the formulae I.A.1 to I.A.6, wherein the substituents $R^{x3}$ and $R^{x4}$ are independently from each other selected from the group consisting of hydrogen or together with the carbon atom, to which they are bound, form a carbonyl group. Most preferably $R^{x3}$ and $R^{x4}$ are hydrogen.

Preference is also given to compounds of the formulae I.A.1 and I.A.4, wherein the substituents $R^{x3'}$ and $R^{x4'}$ are independently from each other selected from the group consisting of hydrogen or together with the carbon atom, to which they are bound, form a carbonyl group. Most preferably $R^{x3'}$ and $R^{x4'}$ are hydrogen.

The substituent $R^{x2}$ in the compounds of formulae I.A.2, IA.3, I.A.5 and I.A.6 preferably is hydrogen or $C_1$-$C_4$-alkyl.

The substituents $R^y$, $R^{y'}$ and $R^{y''}$ in compounds of the formulae I.A.1 to I.A.6 are preferably selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy. More preferably $R^y$, $R^{y'}$ and $R^{y''}$ are hydrogen or halogen. Most preferably $R^y$, $R^{y'}$ and $R^{y''}$ are hydrogen.

Very preferred examples of substituents A in formulae I.A.1 to I.A.6 are phenyl, 2-fluorophenyl, 3-fluorophenyl, 2,3-difluoro-phenyl, 3,4-difluorophenyl, 3,5-difluorophenyl, 2-chlororophenyl, 3-chlorophenyl, 2,3-dichloro-phenyl, 3,4-dichlorophenyl, 3,5-dichlorophenyl, 2-difluoromethylphenyl, 3-difluoromethylphenyl, 2-trifluoromethylphenyl, 3-trifluoromethylphenyl, 2-difluoromethoxyphenyl, 3-difluoromethoxyphenyl, 2-trifluoromethoxyphenyl and 3-trifluoromethoxyphenyl.

According to a second embodiment of the present invention ----- in formula (I) is a double bond. In this embodiment the compounds of formula I are preferably selected from compounds of the formulae I.B.1 to I.B.8

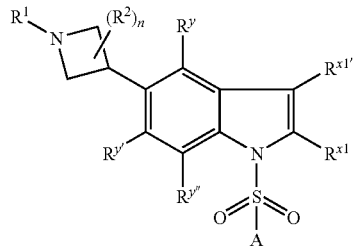
(I.B.1)

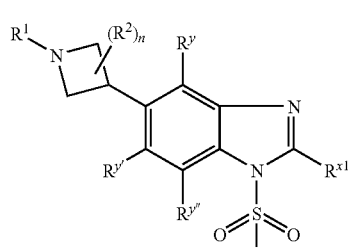
(I.B.2)

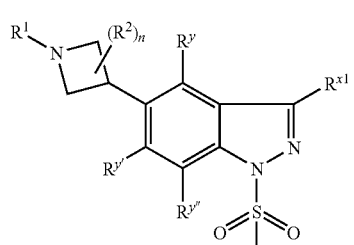
(I.B.3)

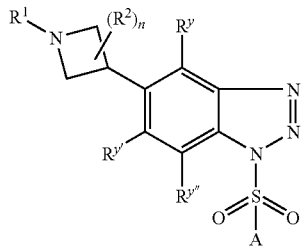
(I.B.4)

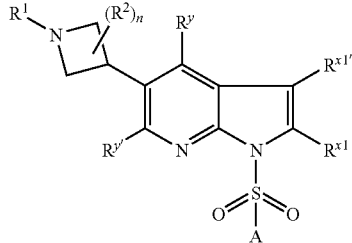
(I.B.5)

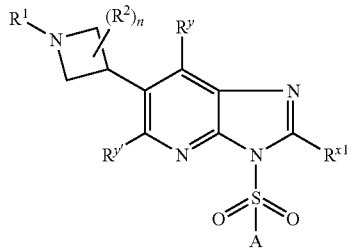
(I.B.6)

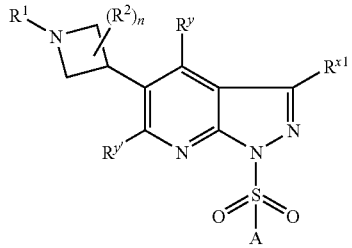
(I.B.7)

(I.B.8)

wherein the radicals A, $R^1$, $R^2$ and n have one the meanings given before, $R^{x1}$ and $R^{x1'}$ independently from each other have one the meanings given for $R^{x1}$ before and $R^y$, $R^{y'}$ and $R^{y''}$ independently from each other have one the meanings given for $R^y$ before.

Particular preference is given to compounds of formula I.B.1.

Particular preference is also given to compounds of formula I.B.5.

The radical $R^1$ in the compounds of the formulae I.B.1 to I.B.8 is preferably selected from the group consisting of hydrogen, $C_1$-$C_4$-alkyl, $C_1$-$C_4$-haloalkyl and $C_3$-$C_6$-cycloalkyl. More preferably the radical $R^1$ is hydrogen.

The radical $R^2$ in the compounds of the formulae I.B.1 to I.B.8 preferably is $C_1$-$C_4$-alkyl. More preferably $R^2$ is methyl.

The azetidin moiety in the compounds of the formulae I.B.1 to I.B.8 is preferably selected from the moieties of formulae AZ.1, AZ.2, AZ.3, AZ.4 and AZ.5.

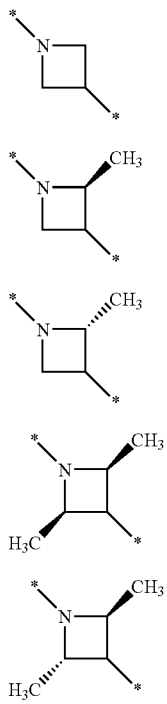

(AZ.1)

(AZ.2)

(AZ.3)

(AZ.4)

(AZ.5)

More preferably azetidin moiety is AZ.1. Thus, n preferably is 0.

A preferred embodiment of the present application relates to compounds of formulae I.B.1 to I.B.8, wherein A is phenyl, which is unsubstituted or may carry 1, 2 or 3 substituents $R^a$.

Preference is given to compounds of the formulae I.B.1 to I.B.86, wherein A is phenyl, which is unsubstituted or may carry 1, 2 or 3 substituents $R^a$, wherein the substituents $R^a$ are attached to the phenyl ring in ortho- and/or meta-position relative to the bonding-position. Very preferred are compounds of formulae I.A.1 to I.A.6, wherein the substituent A is phenyl, which is substituted in the meta-position.

Preference is also given to compounds of the formulae I.B.1 to I.B.8, wherein the radicals $R^a$ are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy. More preference is given to compounds of formulae I.A.1 to I.A.6, wherein the radicals $R^a$ are independently from each other selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

Preference is also given to compounds of the formulae I.B.1 to I.B.3 and I.B.5 to I.B.8, wherein the substituents $R^{x1}$ and $R^{x1'}$ are independently from each other selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy. More preferably $R^{x1}$ and $R^{x1'}$ are selected from hydrogen, halogen and CN. In particular $R^{x1}$ in formulae I.B.1, I.B.2, I.B.5, I.B.6 and I.B.8 is hydrogen, while $R^{x1}$ in formulae I.B.3 and I.B.7 is hydrogen or halogen such as fluorine or chlorine. $R^{x1'}$ in formulae I.B.1 and I.B.5 is in particular hydrogen or halogen, such as fluorine or chlorine. Most preferably $R^{x1}$ and $R^{x1'}$ are hydrogen.

The substituent $R^{x2}$ in the compounds of formulae I.A.2, I.A.3, I.A.5 and I.A.6 preferably is hydrogen or $C_1$-$C_4$-alkyl.

The substituents $R^y$, $R^{y'}$ and $R^{y''}$ in compounds of the formulae I.B.1 to I.B.8 are preferably selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy. More preferably $R^y$, $R^{y'}$ and $R^{y''}$ are hydrogen or halogen. Most preferably $R^y$, $R^{y'}$ and $R^{y''}$ are hydrogen.

Very preferred examples of substituents A in formulae I.B.1 to I.B.8 are phenyl, 2-fluorophenyl, 3-fluorophenyl, 2,3-difluoro-phenyl, 3,4-difluorophenyl, 3,5-difluorophenyl, 2-chlororophenyl, 3-chlorophenyl, 2,3-dichloro-phenyl, 3,4-dichlorophenyl, 3,5-dichlorophenyl, 2-difluoromethylphenyl, 3-difluoromethylphenyl, 2-trifluoromethylphenyl, 3-trifluoromethylphenyl, 2-difluoromethoxyphenyl, 3-difluoromethoxyphenyl, 2-trifluoromethoxyphenyl and 3-trifluoromethoxyphenyl.

Examples of preferred compounds which are represented by the formulae I.A.1, I.A.2, I.A.3, I.A.4, I.A.5, I.A.6, I.B.1, I.B.2, I.B.3, I.B.4, I.B.5, I.B.6, I.B.7 and I.B.8 are the individual compounds listed in tables 1 to 28, wherein the variables A and $(R^2)_n$ have the meanings given in one of rows 1 to 330 of table A.

Table 1.

Compounds of formula I.A.1, wherein $R^y$, $R^{y'}$, $R^{y''}$, $R^{x3}$, $R^{x4}$, $R^{x3'}$ and $R^{x4'}$ are each hydrogen and the variables A, $R^1$ and $(R^2)_n$ have the meanings given in one of rows 1 to 330 of table A (compounds I.1 to I.330).

TABLE A

| | A | $R^1$ | $(R^2)_n$ |
|---|---|---|---|
| 1 | phenyl | H | — |
| 2 | 2-fluorophenyl | H | — |
| 3 | 3-fluorophenyl | H | — |
| 4 | 2,3-difluorphenyl | H | — |
| 5 | 2,4-difluorophenyl | H | — |
| 6 | 2,5-difluorophenyl | H | — |
| 7 | 2,6-difluorophenyl | H | — |
| 8 | 3,4-difluorophenyl | H | — |
| 9 | 3,5-difluorophenyl | H | — |
| 10 | 2-chlorophenyl | H | — |
| 11 | 3-chlorophenyl | H | — |
| 12 | 2-tolyl | H | — |
| 13 | 3-tolyl | H | — |
| 14 | 2-isopropylphenyl | H | — |
| 15 | 3-isopropylphenyl | H | — |
| 16 | 2-difluoromethylphenyl | H | — |
| 17 | 3-difluoromethylphenyl | H | — |
| 18 | 2-trifluoromethylphenyl | H | — |
| 19 | 3-trifluoromethylphenyl | H | — |
| 20 | biphenyl-2-yl | H | — |
| 21 | biphenyl-3-yl | H | — |
| 22 | 2-methoxyphenyl | H | — |
| 23 | 3-methoxyphenyl | H | — |
| 24 | 2-difluoromethoxyphenyl | H | — |
| 25 | 3-difluoromethoxyphenyl | H | — |
| 26 | 2-trifluoromethoxyphenyl | H | — |
| 27 | 3-trifluoromethoxyphenyl | H | — |
| 28 | 2-phenoxyphenyl | H | — |
| 29 | 3-phenoxyphenyl | H | — |
| 30 | 4-(oxazol-5-yl)phenyl | H | — |
| 31 | 3-(pyrrolidin-1-yl)phenyl | H | — |
| 32 | 1-naphtyl | H | — |
| 33 | 2-naphtyl | H | — |
| 34 | pyridin-2-yl | H | — |
| 35 | pyridin-3-yl | H | — |
| 36 | pyridin-4-yl | H | — |
| 37 | 2-(pyrrolidin-1-yl)pyridin-4-yl | H | — |

TABLE A-continued

| | A | R¹ | (R²)ₙ |
|---|---|---|---|
| 38 | 6-morpholinylpyridin-3-yl | H | — |
| 39 | 6-phenoxypyridin-3-yl | H | — |
| 40 | thien-2-yl | H | — |
| 41 | 5-methylthien-2-yl | H | — |
| 42 | 5-(pyridin-2-yl)thien-2-yl | H | — |
| 43 | 5-(2-methylthiazol-4-yl)-thien-2-yl | H | — |
| 44 | 5-chloro-3-methyl-benzo[b]thien-2-yl | H | — |
| 45 | 2-methylthiazol-5-yl | H | — |
| 46 | 2,4-dimethyl-thiazol-5-yl | H | — |
| 47 | 4-methylthiazol-2-yl | H | — |
| 48 | 5-methylthiazol-2-yl | H | — |
| 49 | 3,5-dimethylisoxazol-4-yl | H | — |
| 50 | 1-methylimidazol-4-yl | H | — |
| 51 | benzothiazol-7-yl | H | — |
| 52 | 4-methylbenzomorpholin-8-yl | H | — |
| 53 | quinolin-8-yl | H | — |
| 54 | isoquinolin-4-yl | H | — |
| 55 | 2,1,3-benzoxdiazol-4-yl | H | — |
| 56 | phenyl | H | 2-CH₃ |
| 57 | 2-fluorophenyl | H | 2-CH₃ |
| 58 | 3-fluorophenyl | H | 2-CH₃ |
| 59 | 2,3-difluorphenyl | H | 2-CH₃ |
| 60 | 2,4-difluorophenyl | H | 2-CH₃ |
| 61 | 2,5-difluorophenyl | H | 2-CH₃ |
| 62 | 2,6-difluorophenyl | H | 2-CH₃ |
| 63 | 3,4-difluorophenyl | H | 2-CH₃ |
| 64 | 3,5-difluorophenyl | H | 2-CH₃ |
| 65 | 2-chlorophenyl | H | 2-CH₃ |
| 66 | 3-chlorophenyl | H | 2-CH₃ |
| 67 | 2-tolyl | H | 2-CH₃ |
| 68 | 3-tolyl | H | 2-CH₃ |
| 69 | 2-isopropylphenyl | H | 2-CH₃ |
| 70 | 3-isopropylphenyl | H | 2-CH₃ |
| 71 | 2-difluoromethylphenyl | H | 2-CH₃ |
| 72 | 3-difluoromethylphenyl | H | 2-CH₃ |
| 73 | 2-trifluoromethylphenyl | H | 2-CH₃ |
| 74 | 3-trifluoromethylphenyl | H | 2-CH₃ |
| 75 | biphenyl-2-yl | H | 2-CH₃ |
| 76 | biphenyl-3-yl | H | 2-CH₃ |
| 77 | 2-methoxyphenyl | H | 2-CH₃ |
| 78 | 3-methoxyphenyl | H | 2-CH₃ |
| 79 | 2-difluoromethoxyphenyl | H | 2-CH₃ |
| 80 | 3-difluoromethoxyphenyl | H | 2-CH₃ |
| 81 | 2-trifluoromethoxyphenyl | H | 2-CH₃ |
| 82 | 3-trifluoromethoxyphenyl | H | 2-CH₃ |
| 83 | 2-phenoxyphenyl | H | 2-CH₃ |
| 84 | 3-phenoxyphenyl | H | 2-CH₃ |
| 85 | 4-(oxazol-5-yl)phenyl | H | 2-CH₃ |
| 86 | 3-(pyrrolidin-1-yl)phenyl | H | 2-CH₃ |
| 87 | 1-naphtyl | H | 2-CH₃ |
| 88 | 2-naphtyl | H | 2-CH₃ |
| 89 | pyridin-2-yl | H | 2-CH₃ |
| 90 | pyridin-3-yl | H | 2-CH₃ |
| 91 | pyridin-4-yl | H | 2-CH₃ |
| 92 | 2-(pyrrolidin-1-yl)pyridin-4-yl | H | 2-CH₃ |
| 93 | 6-morpholinylpyridin-3-yl | H | 2-CH₃ |
| 94 | 6-phenoxypyridin-3-yl | H | 2-CH₃ |
| 95 | thien-2-yl | H | 2-CH₃ |
| 96 | 5-methylthien-2-yl | H | 2-CH₃ |
| 97 | 5-(pyridin-2-yl)thien-2-yl | H | 2-CH₃ |
| 98 | 5-(2-methylthiazol-4-yl)-thien-2-yl | H | 2-CH₃ |
| 99 | 5-chloro-3-methyl-benzo[b]thien-2-yl | H | 2-CH₃ |
| 100 | 2-methylthiazol-5-yl | H | 2-CH₃ |
| 101 | 2,4-dimethyl-thiazol-5-yl | H | 2-CH₃ |
| 102 | 4-methylthiazol-2-yl | H | 2-CH₃ |
| 103 | 5-methylthiazol-2-yl | H | 2-CH₃ |
| 104 | 3,5-dimethylisoxazol-4-yl | H | 2-CH₃ |
| 105 | 1-methylimidazol-4-yl | H | 2-CH₃ |
| 106 | benzothiazol-7-yl | H | 2-CH₃ |
| 107 | 4-methylbenzomorpholin-8-yl | H | 2-CH₃ |
| 108 | quinolin-8-yl | H | 2-CH₃ |
| 109 | isoquinolin-4-yl | H | 2-CH₃ |
| 110 | 2,1,3-benzoxdiazol-4-yl | H | 2-CH₃ |
| 111 | phenyl | H | 2-CH₃; 4-CH₃ |
| 112 | 2-fluorophenyl | H | 2-CH₃; 4-CH₃ |
| 113 | 3-fluorophenyl | H | 2-CH₃; 4-CH₃ |
| 114 | 2,3-difluorphenyl | H | 2-CH₃; 4-CH₃ |
| 115 | 2,4-difluorophenyl | H | 2-CH₃; 4-CH₃ |
| 116 | 2,5-difluorophenyl | H | 2-CH₃; 4-CH₃ |
| 117 | 2,6-difluorophenyl | H | 2-CH₃; 4-CH₃ |
| 118 | 3,4-difluorophenyl | H | 2-CH₃; 4-CH₃ |
| 119 | 3,5-difluorophenyl | H | 2-CH₃; 4-CH₃ |
| 120 | 2-chlorophenyl | H | 2-CH₃; 4-CH₃ |
| 121 | 3-chlorophenyl | H | 2-CH₃; 4-CH₃ |
| 122 | 2-tolyl | H | 2-CH₃; 4-CH₃ |
| 123 | 3-tolyl | H | 2-CH₃; 4-CH₃ |
| 124 | 2-isopropylphenyl | H | 2-CH₃; 4-CH₃ |
| 125 | 3-isopropylphenyl | H | 2-CH₃; 4-CH₃ |
| 126 | 2-difluoromethylphenyl | H | 2-CH₃; 4-CH₃ |
| 127 | 3-difluoromethylphenyl | H | 2-CH₃; 4-CH₃ |
| 128 | 2-trifluoromethylphenyl | H | 2-CH₃; 4-CH₃ |
| 129 | 3-trifluoromethylphenyl | H | 2-CH₃; 4-CH₃ |
| 130 | biphenyl-2-yl | H | 2-CH₃; 4-CH₃ |
| 131 | biphenyl-3-yl | H | 2-CH₃; 4-CH₃ |
| 132 | 2-methoxyphenyl | H | 2-CH₃; 4-CH₃ |
| 133 | 3-methoxyphenyl | H | 2-CH₃; 4-CH₃ |
| 134 | 2-difluoromethoxyphenyl | H | 2-CH₃; 4-CH₃ |
| 135 | 3-difluoromethoxyphenyl | H | 2-CH₃; 4-CH₃ |
| 136 | 2-trifluoromethoxyphenyl | H | 2-CH₃; 4-CH₃ |
| 137 | 3-trifluoromethoxyphenyl | H | 2-CH₃; 4-CH₃ |
| 138 | 2-phenoxyphenyl | H | 2-CH₃; 4-CH₃ |
| 139 | 3-phenoxyphenyl | H | 2-CH₃; 4-CH₃ |
| 140 | 4-(oxazol-5-yl)phenyl | H | 2-CH₃; 4-CH₃ |
| 141 | 3-(pyrrolidin-1-yl)phenyl | H | 2-CH₃; 4-CH₃ |
| 142 | 1-naphtyl | H | 2-CH₃; 4-CH₃ |
| 143 | 2-naphtyl | H | 2-CH₃; 4-CH₃ |
| 144 | pyridin-2-yl | H | 2-CH₃; 4-CH₃ |
| 145 | pyridin-3-yl | H | 2-CH₃; 4-CH₃ |
| 146 | pyridin-4-yl | H | 2-CH₃; 4-CH₃ |
| 147 | 2-(pyrrolidin-1-yl)pyridin-4-yl | H | 2-CH₃; 4-CH₃ |
| 148 | 6-morpholinylpyridin-3-yl | H | 2-CH₃; 4-CH₃ |
| 149 | 6-phenoxypyridin-3-yl | H | 2-CH₃; 4-CH₃ |
| 150 | thien-2-yl | H | 2-CH₃; 4-CH₃ |
| 151 | 5-methylthien-2-yl | H | 2-CH₃; 4-CH₃ |
| 152 | 5-(pyridin-2-yl)thien-2-yl | H | 2-CH₃; 4-CH₃ |
| 153 | 5-(2-methylthiazol-4-yl)-thien-2-yl | H | 2-CH₃; 4-CH₃ |
| 154 | 5-chloro-3-methyl-benzo[b]thien-2-yl | H | 2-CH₃; 4-CH₃ |
| 155 | 2-methylthiazol-5-yl | H | 2-CH₃; 4-CH₃ |
| 156 | 2,4-dimethyl-thiazol-5-yl | H | 2-CH₃; 4-CH₃ |
| 157 | 4-methylthiazol-2-yl | H | 2-CH₃; 4-CH₃ |
| 158 | 5-methylthiazol-2-yl | H | 2-CH₃; 4-CH₃ |
| 159 | 3,5-dimethylisoxazol-4-yl | H | 2-CH₃; 4-CH₃ |
| 160 | 1-methylimidazol-4-yl | H | 2-CH₃; 4-CH₃ |
| 161 | benzothiazol-7-yl | H | 2-CH₃; 4-CH₃ |
| 162 | 4-methylbenzomorpholin-8-yl | H | 2-CH₃; 4-CH₃ |
| 163 | quinolin-8-yl | H | 2-CH₃; 4-CH₃ |
| 164 | isoquinolin-4-yl | H | 2-CH₃; 4-CH₃ |
| 165 | 2,1,3-benzoxdiazol-4-yl | H | 2-CH₃; 4-CH₃ |
| 166 | phenyl | n-propyl | — |
| 167 | 2-fluorophenyl | n-propyl | — |
| 168 | 3-fluorophenyl | n-propyl | — |
| 169 | 2,3-difluorphenyl | n-propyl | — |
| 170 | 2,4-difluorophenyl | n-propyl | — |
| 171 | 2,5-difluorophenyl | n-propyl | — |
| 172 | 2,6-difluorophenyl | n-propyl | — |
| 173 | 3,4-difluorophenyl | n-propyl | — |
| 174 | 3,5-difluorophenyl | n-propyl | — |
| 175 | 2-chlorophenyl | n-propyl | — |
| 176 | 3-chlorophenyl | n-propyl | — |
| 177 | 2-tolyl | n-propyl | — |
| 178 | 3-tolyl | n-propyl | — |
| 179 | 2-isopropylphenyl | n-propyl | — |
| 180 | 3-isopropylphenyl | n-propyl | — |
| 181 | 2-difluoromethylphenyl | n-propyl | — |
| 182 | 3-difluoromethylphenyl | n-propyl | — |
| 183 | 2-trifluoromethylphenyl | n-propyl | — |
| 184 | 3-trifluoromethylphenyl | n-propyl | — |
| 185 | biphenyl-2-yl | n-propyl | — |
| 186 | biphenyl-3-yl | n-propyl | — |
| 187 | 2-methoxyphenyl | n-propyl | — |

TABLE A-continued

| | A | R¹ | (R²)ₙ |
|---|---|---|---|
| 188 | 3-methoxyphenyl | n-propyl | — |
| 189 | 2-difluoromethoxyphenyl | n-propyl | — |
| 190 | 3-difluoromethoxyphenyl | n-propyl | — |
| 191 | 2-trifluoromethoxyphenyl | n-propyl | — |
| 192 | 3-trifluoromethoxyphenyl | n-propyl | — |
| 193 | 2-phenoxyphenyl | n-propyl | — |
| 194 | 3-phenoxyphenyl | n-propyl | — |
| 195 | 4-(oxazol-5-yl)phenyl | n-propyl | — |
| 196 | 3-(pyrrolidin-1-yl)phenyl | n-propyl | — |
| 197 | 1-naphtyl | n-propyl | — |
| 198 | 2-naphtyl | n-propyl | — |
| 199 | pyridin-2-yl | n-propyl | — |
| 200 | pyridin-3-yl | n-propyl | — |
| 201 | pyridin-4-yl | n-propyl | — |
| 202 | 2-(pyrrolidin-1-yl)pyridin-4-yl | n-propyl | — |
| 203 | 6-morpholinylpyridin-3-yl | n-propyl | — |
| 204 | 6-phenoxypyridin-3-yl | n-propyl | — |
| 205 | thien-2-yl | n-propyl | — |
| 206 | 5-methylthien-2-yl | n-propyl | — |
| 207 | 5-(pyridin-2-yl)thien-2-yl | n-propyl | — |
| 208 | 5-(2-methylthiazol-4-yl)-thien-2-yl | n-propyl | — |
| 209 | 5-chloro-3-methyl-benzo[b]thien-2-yl | n-propyl | — |
| 210 | 2-methylthiazol-5-yl | n-propyl | — |
| 211 | 2,4-dimethyl-thiazol-5-yl | n-propyl | — |
| 212 | 4-methylthiazol-2-yl | n-propyl | — |
| 213 | 5-methylthiazol-2-yl | n-propyl | — |
| 214 | 3,5-dimethylisoxazol-4-yl | n-propyl | — |
| 215 | 1-methylimidazol-4-yl | n-propyl | — |
| 216 | benzothiazol-7-yl | n-propyl | — |
| 217 | 4-methylbenzomorpholin-8-yl | n-propyl | — |
| 218 | quinolin-8-yl | n-propyl | — |
| 219 | isoquinolin-4-yl | n-propyl | — |
| 220 | 2,1,3-benzoxdiazol-4-yl | n-propyl | — |
| 221 | phenyl | n-propyl | 2-CH₃ |
| 222 | 2-fluorophenyl | n-propyl | 2-CH₃ |
| 223 | 3-fluorophenyl | n-propyl | 2-CH₃ |
| 224 | 2,3-difluorphenyl | n-propyl | 2-CH₃ |
| 225 | 2,4-difluorophenyl | n-propyl | 2-CH₃ |
| 226 | 2,5-difluorophenyl | n-propyl | 2-CH₃ |
| 227 | 2,6-difluorophenyl | n-propyl | 2-CH₃ |
| 228 | 3,4-difluorophenyl | n-propyl | 2-CH₃ |
| 229 | 3,5-difluorophenyl | n-propyl | 2-CH₃ |
| 230 | 2-chlorophenyl | n-propyl | 2-CH₃ |
| 231 | 3-chlorophenyl | n-propyl | 2-CH₃ |
| 232 | 2-tolyl | n-propyl | 2-CH₃ |
| 233 | 3-tolyl | n-propyl | 2-CH₃ |
| 234 | 2-isopropylphenyl | n-propyl | 2-CH₃ |
| 235 | 3-isopropylphenyl | n-propyl | 2-CH₃ |
| 236 | 2-difluoromethylphenyl | n-propyl | 2-CH₃ |
| 237 | 3-difluoromethylphenyl | n-propyl | 2-CH₃ |
| 238 | 2-trifluoromethylphenyl | n-propyl | 2-CH₃ |
| 239 | 3-trifluoromethylphenyl | n-propyl | 2-CH₃ |
| 240 | biphenyl-2-yl | n-propyl | 2-CH₃ |
| 241 | biphenyl-3-yl | n-propyl | 2-CH₃ |
| 242 | 2-methoxyphenyl | n-propyl | 2-CH₃ |
| 243 | 3-methoxyphenyl | n-propyl | 2-CH₃ |
| 244 | 2-difluoromethoxyphenyl | n-propyl | 2-CH₃ |
| 245 | 3-difluoromethoxyphenyl | n-propyl | 2-CH₃ |
| 246 | 2-trifluoromethoxyphenyl | n-propyl | 2-CH₃ |
| 247 | 3-trifluoromethoxyphenyl | n-propyl | 2-CH₃ |
| 248 | 2-phenoxyphenyl | n-propyl | 2-CH₃ |
| 249 | 3-phenoxyphenyl | n-propyl | 2-CH₃ |
| 250 | 4-(oxazol-5-yl)phenyl | n-propyl | 2-CH₃ |
| 251 | 3-(pyrrolidin-1-yl)phenyl | n-propyl | 2-CH₃ |
| 252 | 1-naphtyl | n-propyl | 2-CH₃ |
| 253 | 2-naphtyl | n-propyl | 2-CH₃ |
| 254 | pyridin-2-yl | n-propyl | 2-CH₃ |
| 255 | pyridin-3-yl | n-propyl | 2-CH₃ |
| 256 | pyridin-4-yl | n-propyl | 2-CH₃ |
| 257 | 2-(pyrrolidin-1-yl)pyridin-4-yl | n-propyl | 2-CH₃ |
| 258 | 6-morpholinylpyridin-3-yl | n-propyl | 2-CH₃ |
| 259 | 6-phenoxypyridin-3-yl | n-propyl | 2-CH₃ |
| 260 | thien-2-yl | n-propyl | 2-CH₃ |
| 261 | 5-methylthien-2-yl | n-propyl | 2-CH₃ |
| 262 | 5-(pyridin-2-yl)thien-2-yl | n-propyl | 2-CH₃ |
| 263 | 5-(2-methylthiazol-4-yl)-thien-2-yl | n-propyl | 2-CH₃ |
| 264 | 5-chloro-3-methyl-benzo[b]thien-2-yl | n-propyl | 2-CH₃ |
| 265 | 2-methylthiazol-5-yl | n-propyl | 2-CH₃ |
| 266 | 2,4-dimethyl-thiazol-5-yl | n-propyl | 2-CH₃ |
| 267 | 4-methylthiazol-2-yl | n-propyl | 2-CH₃ |
| 268 | 5-methylthiazol-2-yl | n-propyl | 2-CH₃ |
| 269 | 3,5-dimethylisoxazol-4-yl | n-propyl | 2-CH₃ |
| 270 | 1-methylimidazol-4-yl | n-propyl | 2-CH₃ |
| 271 | benzothiazol-7-yl | n-propyl | 2-CH₃ |
| 272 | 4-methylbenzomorpholin-8-yl | n-propyl | 2-CH₃ |
| 273 | quinolin-8-yl | n-propyl | 2-CH₃ |
| 274 | isoquinolin-4-yl | n-propyl | 2-CH₃ |
| 275 | 2,1,3-benzoxdiazol-4-yl | n-propyl | 2-CH₃ |
| 276 | phenyl | n-propyl | 2-CH₃; 4-CH₃ |
| 277 | 2-fluorophenyl | n-propyl | 2-CH₃; 4-CH₃ |
| 278 | 3-fluorophenyl | n-propyl | 2-CH₃; 4-CH₃ |
| 279 | 2,3-difluorphenyl | n-propyl | 2-CH₃; 4-CH₃ |
| 280 | 2,4-difluorophenyl | n-propyl | 2-CH₃; 4-CH₃ |
| 281 | 2,5-difluorophenyl | n-propyl | 2-CH₃; 4-CH₃ |
| 282 | 2,6-difluorophenyl | n-propyl | 2-CH₃; 4-CH₃ |
| 283 | 3,4-difluorophenyl | n-propyl | 2-CH₃; 4-CH₃ |
| 284 | 3,5-difluorophenyl | n-propyl | 2-CH₃; 4-CH₃ |
| 285 | 2-chlorophenyl | n-propyl | 2-CH₃; 4-CH₃ |
| 286 | 3-chlorophenyl | n-propyl | 2-CH₃; 4-CH₃ |
| 287 | 2-tolyl | n-propyl | 2-CH₃; 4-CH₃ |
| 288 | 3-tolyl | n-propyl | 2-CH₃; 4-CH₃ |
| 289 | 2-isopropylphenyl | n-propyl | 2-CH₃; 4-CH₃ |
| 290 | 3-isopropylphenyl | n-propyl | 2-CH₃; 4-CH₃ |
| 291 | 2-difluoromethylphenyl | n-propyl | 2-CH₃; 4-CH₃ |
| 292 | 3-difluoromethylphenyl | n-propyl | 2-CH₃; 4-CH₃ |
| 293 | 2-trifluoromethylphenyl | n-propyl | 2-CH₃; 4-CH₃ |
| 294 | 3-trifluoromethylphenyl | n-propyl | 2-CH₃; 4-CH₃ |
| 295 | biphenyl-2-yl | n-propyl | 2-CH₃; 4-CH₃ |
| 296 | biphenyl-3-yl | n-propyl | 2-CH₃; 4-CH₃ |
| 297 | 2-methoxyphenyl | n-propyl | 2-CH₃; 4-CH₃ |
| 298 | 3-methoxyphenyl | n-propyl | 2-CH₃; 4-CH₃ |
| 299 | 2-difluoromethoxyphenyl | n-propyl | 2-CH₃; 4-CH₃ |
| 300 | 3-difluoromethoxyphenyl | n-propyl | 2-CH₃; 4-CH₃ |
| 301 | 2-trifluoromethoxyphenyl | n-propyl | 2-CH₃; 4-CH₃ |
| 302 | 3-trifluoromethoxyphenyl | n-propyl | 2-CH₃; 4-CH₃ |
| 303 | 2-phenoxyphenyl | n-propyl | 2-CH₃; 4-CH₃ |
| 304 | 3-phenoxyphenyl | n-propyl | 2-CH₃; 4-CH₃ |
| 305 | 4-(oxazol-5-yl)phenyl | n-propyl | 2-CH₃; 4-CH₃ |
| 306 | 3-(pyrrolidin-1-yl)phenyl | n-propyl | 2-CH₃; 4-CH₃ |
| 307 | 1-naphtyl | n-propyl | 2-CH₃; 4-CH₃ |
| 308 | 2-naphtyl | n-propyl | 2-CH₃; 4-CH₃ |
| 309 | pyridin-2-yl | n-propyl | 2-CH₃; 4-CH₃ |
| 310 | pyridin-3-yl | n-propyl | 2-CH₃; 4-CH₃ |
| 311 | pyridin-4-yl | n-propyl | 2-CH₃; 4-CH₃ |
| 312 | 2-(pyrrolidin-1-yl)pyridin-4-yl | n-propyl | 2-CH₃; 4-CH₃ |
| 313 | 6-morpholinylpyridin-3-yl | n-propyl | 2-CH₃; 4-CH₃ |
| 314 | 6-phenoxypyridin-3-yl | n-propyl | 2-CH₃; 4-CH₃ |
| 315 | thien-2-yl | n-propyl | 2-CH₃; 4-CH₃ |
| 316 | 5-methylthien-2-yl | n-propyl | 2-CH₃; 4-CH₃ |
| 317 | 5-(pyridin-2-yl)thien-2-yl | n-propyl | 2-CH₃; 4-CH₃ |
| 318 | 5-(2-methylthiazol-4-yl)-thien-2-yl | n-propyl | 2-CH₃; 4-CH₃ |
| 319 | 5-chloro-3-methyl-benzo[b]thien-2-yl | n-propyl | 2-CH₃; 4-CH₃ |
| 320 | 2-methylthiazol-5-yl | n-propyl | 2-CH₃; 4-CH₃ |
| 321 | 2,4-dimethyl-thiazol-5-yl | n-propyl | 2-CH₃; 4-CH₃ |
| 322 | 4-methylthiazol-2-yl | n-propyl | 2-CH₃; 4-CH₃ |
| 323 | 5-methylthiazol-2-yl | n-propyl | 2-CH₃; 4-CH₃ |
| 324 | 3,5-dimethylisoxazol-4-yl | n-propyl | 2-CH₃; 4-CH₃ |
| 325 | 1-methylimidazol-4-yl | n-propyl | 2-CH₃; 4-CH₃ |
| 326 | benzothiazol-7-yl | n-propyl | 2-CH₃; 4-CH₃ |
| 327 | 4-methylbenzomorpholin-8-yl | n-propyl | 2-CH₃; 4-CH₃ |
| 328 | quinolin-8-yl | n-propyl | 2-CH₃; 4-CH₃ |
| 329 | isoquinolin-4-yl | n-propyl | 2-CH₃; 4-CH₃ |
| 330 | 2,1,3-benzoxdiazol-4-yl | n-propyl | 2-CH₃; 4-CH₃ |

Table 2.

Compounds of formula I.A.2, wherein $R^y$, $R^{y'}$, $R^{y''}$, $R^{x2}$, $R^{x3}$ and $R^{x4}$ are each hydrogen and the variables A, R¹ and $(R^2)_n$ have the meanings given in one of rows 1 to 330 of table A (compounds I.331 to I.660).

Table 3.

Compounds of formula I.A.3, $R^y$, $R^{y'}$, $R^{y''}$, $R^{x2}$, $R^{x3}$ and $R^{x4}$ are each hydrogen and the variables A, $R^1$ and $(R^2)_n$ have the meanings given in one of rows 1 to 330 of table A (compounds I.661 to I.990).

Table 4.

Compounds of formula I.A.4, wherein $R^y$, $R^{y'}$, $R^{x3}$, $R^{x4}$, $R^{x3'}$ and $R^{x4'}$ are each hydrogen and the variables A, $R^1$ and $(R^2)_n$ have the meanings given in one of rows 1 to 330 of table A (compounds I.991 to I.1320).

Table 5.

Compounds of formula I.A.5, wherein $R^y$, $R^{y'}$, $R^{x2}$, $R^{x3}$ and $R^{x4}$ are each hydrogen and the variables A, $R^1$ and $(R^2)_n$ have the meanings given in one of rows 1 to 330 of table A (compounds I.1321 to I.1650).

Table 6.

Compounds of formula I.A.6, wherein $R^y$, $R^{y'}$, $R^{x2}$, $R^{x3}$ and $R^{x4}$ are each hydrogen and the variables A, $R^1$ and $(R^2)_n$ have the meanings given in one of rows 1 to 330 of table A (compounds I.1651 to I.1980).

Table 7.

Compounds of formula I.B.1, wherein $R^y$, $R^{y'}$, $R^{y''}$, $R^{x1}$ and $R^{x1'}$ are each hydrogen and the variables A, $R^1$ and $(R^2)_n$ have the meanings given in one of rows 1 to 330 of table A (compounds I.1981 to I.2310).

Table 8.

Compounds of formula I.B.2, wherein $R^y$, $R^{y'}$, $R^{y''}$ and $R^{x1}$ are each hydrogen and the variables A, $R^1$ and $(R^2)_n$ have the meanings given in one of rows 1 to 330 of table A (compounds I.2311 to I.2640).

Table 9.

Compounds of formula I.B.3, wherein $R^y$, $R^{y'}$, $R^{y''}$ and $R^{x1}$ are each hydrogen and the variables A, $R^1$ and $(R^2)_n$ have the meanings given in one of rows 1 to 330 of table A (compounds I.2641 to I.2970).

Table 10.

Compounds of formula I.B.4, wherein $R^y$, $R^{y'}$ and $R^{y''}$ are each hydrogen and the variables A, $R^1$ and $(R^2)_n$ have the meanings given in one of rows 1 to 330 of table A (compounds I.2971 to I.3300).

Table 11.

Compounds of formula I.B.5, wherein $R^y$, $R^{y'}$, $R^{x1}$ and $R^{x1'}$ are each hydrogen and the variables A, $R^1$ and $(R^2)_n$ have the meanings given in one of rows 1 to 330 of table A (compounds I.3301 to I.3630).

Table 12.

Compounds of formula I.B.6, wherein $R^y$, $R^{y'}$ and $R^{x1}$ are each hydrogen and the variables A, $R^1$ and $(R^2)_n$ have the meanings given in one of rows 1 to 330 of table A (compounds I.3631 to I.3960).

Table 13.

Compounds of formula I.B.7, wherein $R^y$, $R^{y'}$, and $R^{x1}$ are each hydrogen and the variables A, $R^1$ and $(R^2)_n$ have the meanings given in one of rows 1 to 330 of table A (compounds I.3961 to I.4290).

Table 14.

Compounds of formula I.B.8, wherein $R^y$ and $R^{x1}$ are each hydrogen and the variables A, $R^1$ and $(R^2)_n$ have the meanings given in one of rows 1 to 330 of table A (compounds I.4291 to I.4620).

Table 15.

Compounds of formula I.A.1, wherein $R^y$, $R^{y'}$, $R^{y''}$, $R^{x3'}$ and $R^{x4'}$ are each hydrogen, $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.4621 to I.4950).

Table 16.

Compounds of formula I.A.2, wherein $R^y$, $R^{y'}$, $R^{y''}$ and $R^{x2}$ are each hydrogen, $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.4951 to I.5280).

Table 17.

Compounds of formula I.A.4, wherein $R^y$, $R^{y'}$, $R^{x3'}$ and $R^{x4'}$ are each hydrogen, $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.5281 to I.5610).

Table 18.

Compounds of formula I.A.5, wherein $R^y$, $R^{y'}$ and, $R^{x2}$ are each hydrogen, $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.5611 to I.5940).

Table 19.

Compounds of formula I.A.1, wherein $R^y$, $R^{y'}$, $R^{y''}$, $R^{x3}$ and $R^{x4}$ are each hydrogen, $R^{x3'}$ and $R^{x4'}$ together with the carbon atom to which they are bound form a carbonyl group and the variables A, $R^1$ and $(R^2)_n$ have the meanings given in one of rows 1 to 330 of table A (compounds I.5941 to I.6270).

Table 20.

Compounds of formula I.A.3, $R^y$, $R^{y'}$, $R^{y''}$ and $R^{x2}$ are each hydrogen, $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.6271 to I.6600).

Table 21.

Compounds of formula I.A.4, wherein $R^y$, $R^{y'}$, $R^{x3}$ and $R^{x4}$ are each hydrogen, $R^{x3'}$ and $R^{x4'}$ together with the carbon atom to which they are bound form a carbonyl group and the variables A, $R^1$ and $(R^2)_n$ have the meanings given in one of rows 1 to 330 of table A (compounds I.6601 to I.6930).

Table 22.

Compounds of formula I.A.6, wherein $R^y$, $R^{y'}$ and $R^{x2}$ are each hydrogen $R^{x3}$ and $R^{x4}$ together with the carbon atom to which they are bound form a carbonyl group and the variables A, $R^1$ and $(R^2)_n$ have the meanings given in one of rows 1 to 330 of table A (compounds I.6931 to I.7260).

Table 23.

Compounds of formula I.A.1, wherein $R^y$, $R^{y'}$ and $R^{y''}$ are each hydrogen, each $R^{x3}$ and $R^{x4}$, $R^{x3'}$ and $R^{x4'}$ together with the carbon atom to which they are bound form a carbonyl group and the variables A, $R^1$ and $(R^2)_n$ have the meanings given in one of rows 1 to 330 of table A (compounds I.7261 to I.7590).

Table 24.

Compounds of formula I.A.4, wherein $R^y$ and $R^{y'}$ are each hydrogen, each $R^{x3}$ and $R^{x4}$, $R^{x3'}$ and $R^{x4'}$ together with the carbon atom to which they are bound form a carbonyl group and the variables A, $R^1$ and $(R^2)_n$ have the meanings given in one of rows 1 to 330 of table A (compounds I.7591 to I.7920).

Table 25.

Compounds of formula I.B.1, wherein $R^y$, $R^{y'}$, $R^{y''}$ and $R^{x1}$ are each hydrogen, and $R^{x1'}$ is chlorine, and the variables A, $R^1$ and $(R^2)_n$ have the meanings given in one of rows 1 to 330 of table A (compounds I.7921 to I.8250).

Compounds of formula I.B.1, wherein $R^y$, $R^{y'}$, $R^{y''}$ and $R^{x1}$ are each hydrogen, and $R^{x1'}$ is fluorine, and the variables A, $R^1$ and $(R^2)_n$ have the meanings given in one of rows 1 to 330 of table A (compounds I.8251 to I.8580).

Compounds of formula I.B.5, wherein $R^y$, $R^{y'}$ and $R^{x1}$ are each hydrogen, and $R^{x1'}$ is chlorine, and the variables A, $R^1$ and $(R^2)_n$ have the meanings given in one of rows 1 to 330 of table A (compounds I.8581 to I.8910).

Compounds of formula I.B.1, wherein $R^y$, $R^{y'}$ and $R^{x1}$ are each hydrogen, and $R^{x1'}$ is fluorine, and the variables A, $R^1$ and $(R^2)_n$ have the meanings given in one of rows 1 to 330 of table A (compounds I.8911 to I.9240).

Compounds I of the present invention can be obtained as outlined in the synthetic routes A, B and C below.

1. General Synthetic Pathways

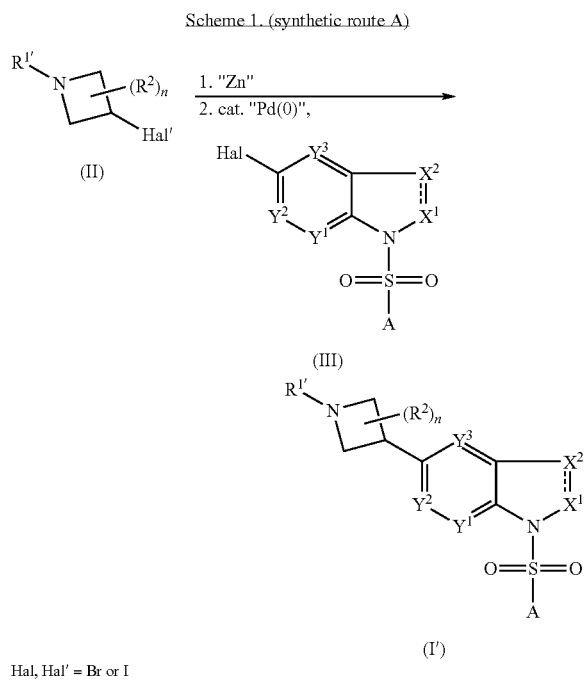

Hal, Hal' = Br or I

In scheme 1 $R^{1'}$ is a radical $R^1$ different from hydrogen or a suitable N-protecting group, e.g. Boc, and Hal and Hal' are halogen, in particular Br or I. According to scheme 1 the halogen compound (II) is converted into a organozinc reagent according to the process described in Tetrahedron 1987, 43, 2203-2212; J. Org. Chem. 1988, 53, 2390-2392 followed by Pd(0)-mediated cross coupling reaction with an appropriate bicyclic halo compound (III) to give the azetidine substituted compound (I') in analogy to the method described in Synlett 1998, 4, 379-380; J. Am. Chem. Soc. 2003, 125, 12527-12530. Alternatively, the intermediately generated organozinc reagent can be converted into a compound of formula (I') via transmetallation, e.g. with CuCn*2LiCl, and subsequent reaction with a compound of formula (III). The free amino function of the azetidin moiety may be regenerated by cleavage of the N—$R^{1'}$-bond (e.g. with trifluoroacetic acid in the case of a Boc carbamate) and subsequently converted into an amide by reaction with the appropriate acyl chloride.

If in the resulting sulfonamide (I') the radical $R^{1'}$ is not the desired radical $R^1$ but a precursor thereof, the compound can be modified as outlined below to obtain the desired substituent $R^1$. A precursor is a radical which can be easily removed and replaced by the desired group $R^1$ or which can be modified to give $R^1$. The precursor can also be an N-protective group (PG), such as butyloxycarbonyl (Boc).

If $R^{1'}$ is allyl, the allyl group can be cleaved to obtain a compound wherein $R^{1'}$ is hydrogen. The cleavage of the allyl group is achieved, for example, by reacting compound (I'-1) [R'=allyl] with an allyl trapping agent, such as mercaptobenzoic acid or 1,3-dimethylbarbituric acid, in the presence of catalytic quantities of palladium (0) compounds or palladium compounds which are able to form a palladium(0) compound under reaction conditions, e.g. palladium dichloride, tetrakis (triphenylphosphine)palladium(0) or tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem. 2002, 67(11) pp. 3718-3723). Alternatively, the cleavage of N-allyl can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

If R' is benzyl, this substituent may also be cleaved to obtain a compound (I'-1) wherein R' is H. The reaction conditions for the cleavage are known in the art. Typically, the benzyl group is removed by a hydrogenation reaction in the presence of a suitable Pd catalyst, such as Pd on carbon or palladium hydroxide.

$R^{1'}$ can also be a protective group. The protective group may be removed to yield a compound (I'-1) wherein R' is H. Suitable protective groups are known in the art and are, for example, selected from tert-butoxycarbonyl (Boc), benzyloxycarbonyl (Cbz), 9-fluorenylmethoxycarbonyl (Fmoc), triphenylmethyl (Trt) and nitrobenzenesulfenyl (Nps). A preferred protective group is Boc. The protective groups can be removed by known methods, such as treatment of the protected amine with an acid, e.g. halogen acid, such as HCl or HBr, formic acid or trifluoroacetic acid, or by hydrogenation, optionally in the presence of a Pd catalyst.

The resulting compound, wherein $R^{1'}$ is H, can then be reacted, in a known manner, in the sense of an alkylation, with a compound $R^1$—X. In this compound, $R^1$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl or $C_3$-$C_6$-cycloalkyl-$C_1$-$C_4$-alkyl and X is a nucleophilically displaceable leaving group, e.g. halogen, trifluoromethylsulfonate, alkylsulfonate, arylsulfonate, alkyl sulfate and the like. The reaction conditions which are required for the alkylation have been adequately disclosed, e.g. in Bioorganic and Medicinal Chemistry Lett. 2002, 12(7), pp. 2443-2446 and also 2002, 12(5), pp. 1917-1919.

The alkylation can also be achieved, in the sense of a reductive amination, by reacting the compound (I'), wherein $R^{1'}$=H, with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Lett. 2002, 12(5), pp. 795-798 and 12(7) pp. 1269-1273.

In case $R^{1'}$ is hydrogen, the resulting sulfonamide (I'-1) can further be reacted with an acyl halide to obtain a compound of the formula I wherein $R^{1'}$ is $C_1$-$C_3$-alkylcarbonyl. The carbonyl group in these compounds can be reduced with diborane to obtain compounds of the general formula I, wherein $R^1$ is $C_2$-$C_4$-alkyl. The carbonyl group can also be reacted with a fluorinating agent to obtain a compound I wherein $R^{1'}$ is 1,1-difluoroalkyl. Acylation and reduction can be achieved by standard methods, which are discussed in Jerry March, Advanced Organic Chemistry, 3rd ed. J. Wiley & Sons, New York 1985, p. 370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

A synthetic route to compounds (III) is outlined in scheme 2.

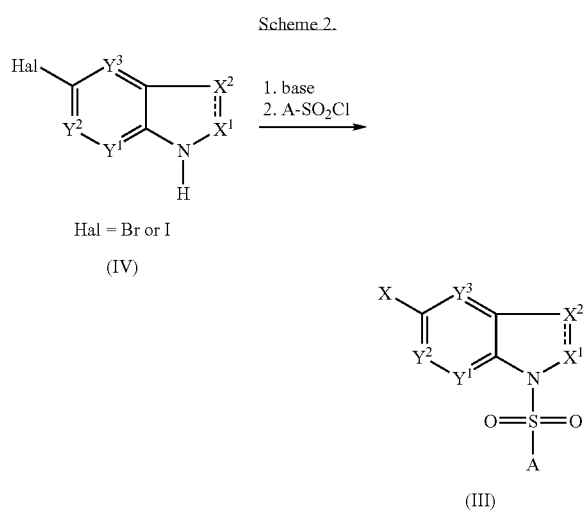

In scheme 1 Hal is halogen, in particular Br or I. Sulfonamide compounds of formula (III) can be obtained by reacting a bicyclic amino compound of formula (IV) with a suitable sulfonic acid derivative. A suitable sulfonic acid derivative is e.g. the sulfonyl chloride A-$SO_2CL$. The sulfonation reaction is preferably carried out in the presence of a base, according to standard procedures in the art. In the reaction depicted in the above scheme 2, the sulfonation takes place under the reaction conditions which are customary for preparing sulfonamide compounds or sulfonic esters, respectively, and which are described, for example, in J. March, Advanced Organic Chemistry, $3^{rd}$ edition, John Wiley & Sons, New York, 1985 page 444ff and the literature cited therein, European J. Org. Chem. 2002 (13), pp. 2094-2108, Tetrahedron 2001, 57 (27) pp. 5885-5895, Bioorganic and Medicinal Chemistry Letters 2000, 10(8), pp. 835-838 and Synthesis 2000 (1), pp. 103-108. The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, an aromatic hydrocarbon, such as toluene, xylene, cumene and the like, a polar aprotic solvent, such as dimethylformamide (DMF), N-methylpyrrolidon (NMP) or acetonitrile, or in a mixture of the above-mentioned solvents. The reaction with A-$SO_2CL$ is customarily carried out in the presence of an auxiliary base. Suitable bases are inorganic bases, such as sodium carbonate or potassium carbonate, or sodium hydrogencarbonate or potassium hydrogencarbonate, alkaline metal hydrides, such as sodium hydride, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amino compound (IV).

The sulfonylchlorides Cl—$SO_2$-A are either commercially available or can be prepared according to standard synthetic methods. One particularly suitable synthetic method for preparing sulfonylchlorides is described in Synthesis 1986, 852-854 or in Tetrahedron Letters 47 (2006), 4125-4128. The sulfonylchlorides are prepared by reacting a halogenated (brominated) aromatic compound with alkyllithium, such as n-butyllithium, to yield a lithiated aromatic compound, which is reacted with sulfur dioxide to yield an aromatic lithium sulfinate compound, which is finally transformed to the corresponding sulfonylchloride by reaction with sulfuryl chloride. Sulfonylchlorides may also be prepared by diazotation of suitable amine precursor A-$NH_2$ with sodium nitrite under acidic conditions and reaction with sulfur dioxide in acetic acid (scheme (iii); J. Org. Chem., 1960, 25, 1824-26); by oxidation of suitable hetaryl-thiols HS-A or hetaryl-benzylthioethers $C_6H_5$—$CH_2$—S-A with chlorine (Synthesis, 1998, 36-38; J. Am. Chem. Soc., 1950, 74, 4890-92) directly to the corresponding sulfonyl chlorides. The further are known in the art or may be prepared by standard methods. Sulfonylchlorides containing a fluorinated radical $R^a$ may be prepared by different synthetic routes, e.g. by reacting suitable hydroxy or oxo precursor (e.g. a compound Cl—$SO_2$-A, carrying a hydroxy or oxo substituted radical) with fluorinating reagents like DAST (diethylaminosulfurtrifluoride), morpholine-DAST, deoxo-fluor (bis(2-methoxyethyl)aminosulfur trifluoride), Ishikawa's reagent (N,N-diethyl-(1,1,2,3,3,3-hexafluoropropyl)amine; Journal of Fluorine Chemistry, 1989, 43, 371-377). More conventionally, the hydroxy group of an aromatic compound which carries a hydroxy substituted radical but not a chlorosulfonyl group, is transformed into a leaving group which is then replace by a fluoride ion (J. Org. Chem., 1994, 59, 2898-22901; Tetrahedron Letters, 1998, 7305-6; J. Org. Chem., 1998, 63, 9587-9589, Synthesis, 1987, 920-21). Subsequent direct chlorosulfonylation with chlorosulfonic acid (Heterocycles, 2001, 55, 9, 1789-1803; J. Org. Chem., 2000, 65, 1399-1406) or a two step process preparing first the sulfonic acid derivatives which are then transformed to the sulfonylchlorides with e.g. chlorosulfonic acid, phosphorous pentachloride (Eur. J. Med. Chem., 2002, 36, 809-828) and the like, yields the desired sulfonylchloride (Tetrahedron Letters, 1991, 33, 50 7787-7788)).

Alternatively compounds I (respectively compounds I') of the present invention can be obtained via synthetic route B as depicted in scheme 3:

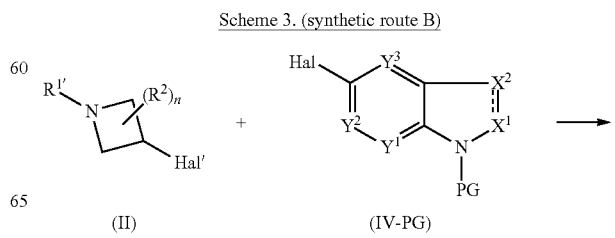

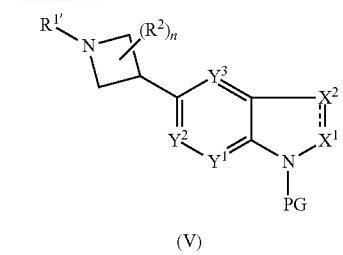

(V)

PG = protecting group (e.g. TiPS)
Hal, Hal' = Br or I

In scheme 3 the variables $R^{1'}$, Hal and Hal' have one of the meanings given in the context of schemes 1 and 2 and PG is a N-protecting group, such as triisopropylsilyl (TiPS). The coupling of compound (II) and compound (IV-PG) can be carried out under the conditions outlined above for the coupling of compounds (II) and (III). Cleavage of the protecting group PG of compound (V) and subsequent sulfonation of the thus liberated amino group using the conditions outlined above for the synthesis of sulfonamides of formula (III) leads to compounds of formula (I').

The substituent A can be varied by either using different sulfonyl chlorides or by modifying the substituents of the group A after the formation of the sulfonamide (I') by known methods. For example, a bromine substituent of the Ar group may be replaced by an N-bound pyrrolidinyl group according to the procedure described in Tetrahedron Asym. 1999, 10, 1831. This Pd-mediated coupling is generally applicable to all nitrogen-containing heterocycles such as azetidinyl, pyrazolidinyl, imidazolidinyl, piperidinyl, piperazinyl, morpholinyl and the like. The reaction is also applicable to heterocyclic compounds carrying one or more substituents such as halogen, alkyl or fluorinated alkyl. A bromine substituent of group A may further be replaced by an isopropenyl group according to a Stille coupling where the bromo compound is reacted with an alkenyl tributyl stannate in the presence of an appropriate Pd coupling catalyst, e.g. tetrakistriphenylphosphine palladium(0) (see, e.g. Tetrahedron, 2003, 59(34), 6545 and Bioorg. Med. Chem. 1999, 7(5), 665). The isopropenyl group may then be converted into the isopropyl group by known hydrogenation methods. Instead of the Stille coupling Suzuki or Suzuki-Miyaura coupling can be used for transmetallation as well. In this case the bromo compound is reacted with an activated boronic acid compound or a derivative thereof, such as an alkenyltrifluoroborate (for conditions see, e.g. J. Org. Chem. 2002, 67, 8424-8429; synthesis 2006, 860-864).

2. Specific Syntheses 2.1 Synthesis of Compounds I, Wherein ----- is a Single Bond, and Precursors Thereof Compounds of formula I (respectively of formula I') wherein ----- is a single bond, in particular compounds of formula I containing a fused dihydro-pyrrole ring, can for instance be prepared as follows.

Scheme 4.

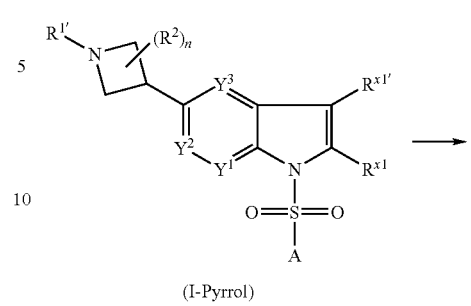

(I-Pyrrol)

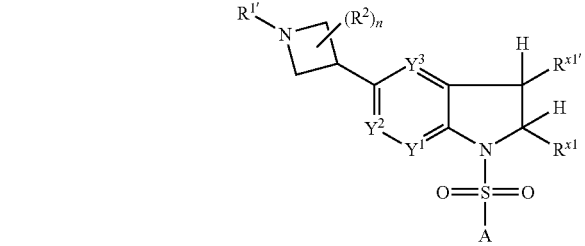

In scheme 4 $R^{1'}$ has one of the meanings given in the context of schemes 1 and 2. Compounds according to the present invention, wherein the bicyclic core is a fused dihydro-pyrrole ring, can be prepared by hydrogenation of the corresponding compound containing a fused pyrrole ring as the bicyclic core. Suitable conditions are for instance described in Chem. Rev. 1969, 69, 785; The chemistry of indoles, academic press, New York, 1970, 129-135; Hetrocyclic compounds, Indoles, Part One, W. J., Ed., Wiley, New York 1972, 163-177 or Comprehensive Organic Chemistry, I. Flemming, Ed., Pergamon, Oxford, Vol. 8. Standard conditions for the hydrogenation would e.g. be dissolving the fused pyrrole compound in an inert solvent such as methanol and reacting it under superatmospheric $H_2$-pressure (e.g. 10 mbar) in the presence of Pd/C. Another method for the reduction of N-(phenylsulfonyl)indoles is described in Tetrahedron Letters, 1989, 30(49), 6833-6836. According to this method N-(phenylsulfonyl)indoles can be transformed into the corresponding 2,3-dihydroindoles by reaction with sodium cyanoborohydride in trifluoroacetic acid. Under these conditions compounds of formula (I-Pyrrole) other than indoles can be reduced as well. Enantioselective hydrogenation of compounds of formula (I-Pyrrole) can for instance be obtained under the conditions outlined in Tetrahedron Assym., 2006, 17, 521-535 using a chiral catalyst.

2.2 Synthesis of Compounds (II) and Precursors Thereof

Compounds of formula II can be synthesized as follows.

Scheme 5.

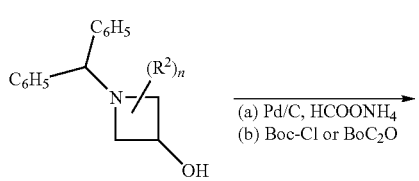

(a) Pd/C, HCOONH$_4$
(b) Boc-Cl or BoC$_2$O

-continued

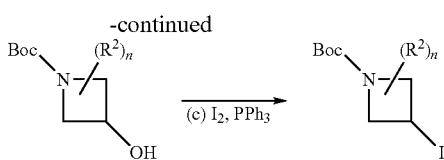

Starting from a 1-benzhydryl-azetidin-3-ol compound, Pd-mediated deprotection of the amine (Tetrahedron 2002, 58, 9865-9870), carbamate formation and subsequent halogenation generate an intermediate iodine compound that is susceptible to undergo Zn insertion (Tetrahedron 1987, 43, 2203-2212; J. Org. Chem. 1988, 53, 2390-2392). The thus obtainable organozinc compound can be used in synthetic routes A or B as outlined above. The synthesis of azetidin-3-ol compounds has for instance been described in J. Med. Chem. 1994, 37, 4195-4210 or Helvetica Chimica Acta 1995, 78, 1238-1246.

3. Synthesis of Enantiomerically Pure Compounds I

Enantiomerically pure compounds (I) can be obtained by applying standard resolution techniques to suitable precursors thereof. For instance, compounds (I') (see scheme 1 above) or compounds (V) (see scheme 3 above), wherein $R^{1'}$ is H or a suitable protective group, such as benzyl, may be reacted with a chiral acid e.g. tartaric acid or a derivative thereof to afford two diastereomeric salts. These can be separated in a customary manner, e.g. by extraction or chromatographic methods or preferably by fractionated crystallization. The thus separated diastereomeric salts are then converted into enantiomerically pure compounds (I') or (V) by reacting the salts with a suitable base to afford the S- or R-enantiomers of compounds (I') or V. Suitable bases are, e.g., alkali metal hydroxides, such as potassium hydroxide and sodium hydroxide, alkaline earth metal hydroxides, such as magnesium hydroxide and calcium hydroxide, alkali metal carbonates, such as sodium carbonate and potassium carbonate, alkaline earth metal carbonates, such as magnesium carbonate and calcium carbonate, alkali metal oxides such as sodium oxide and potassium oxide, and alkaline earth metal oxides, such as magnesium oxide and calcium oxide; organic bases, such as alkoholates, e.g. sodium methanolate, sodium ethanolate or sodium-tert-butanolate, amines, such as dimethylamine, trimethylamine, diethylamine, triethylamine, dipropylamine, tripropylamine, diisopropylamine, diisopropylethylamine and the like, and nitrogen-containing basic heterocyclic compounds, such as pyridine, picoline and lutidine.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example acetonitrile, a lower alcohol, such as methanol, ethanol or propanol, an ether, such as diethyl ether, methyl tert-butyl ether or diisopropyl ether, a ketone, such as acetone or methyl ethyl ketone, an ester, such as ethyl acetate, mixtures thereof as well as mixtures thereof with water.

The compound of the invention can be a 5-$HT_6$ receptor agonist, including partial agonistic activity, or a 5-$HT_6$ receptor antagonist, including inverse agonist activity.

The compounds of formula I according to the present invention have a surprisingly high affinity for 5-$HT_6$ receptors. The high affinity of the compounds according to the invention for 5-$HT_6$ receptors is reflected in very low in-vitro receptor binding constants ($K_i$(5-$HT_6$) values) of as a rule less than 50 nM (nmol/l), preferably of less than 10 nM and, in particular of less than 5 nM. The displacement of $^3$H-LSD can, for example, be used in receptor binding studies for determining binding affinities to 5-$HT_6$ receptors.

Furthermore the compounds of formula I are highly selective 5-$HT_6$ receptor ligands which, because of their low affinity for other receptors such as dopamine receptors, adrenergic receptors, muscarinic receptors, histamine receptors, opiate receptors, in particular dopamine $D_2$, $_1$-adrenergic and histamine $H_1$ receptors, give rise to fewer side-effects than other, less selective 5-$HT_6$ ligands.

For instance the 5-$HT_6$/$D_2$, 5-$HT_6$/$_1$-adrenergic or 5-$HT_6$/$H_1$ selectivities of the compounds according to the present invention, i.e. the ratios $K_i(D_2)/K_i$(5-$HT_6$), $K_i$(1-adrenergic)/$K_i$(5-$HT_6$) or $K_i(H_1)/K_i$(5-$HT_6$) of the receptor binding constants, is as a rule at least 25, preferably at least 50, even better at least 100.

The displacement of [$^3$H]SCH23390 or [$^{125}$I]spiperone can be used, for example, for carrying out receptor binding studies on $D_1$, $D_2$ and $D_4$ receptors.

Furthermore the compounds of formula I because of their structural features are susceptible to display an enhanced brain penetration than other known 5-$HT_6$ receptor ligands.

Because of their binding profile, the compounds can be used for treating diseases which respond to 5-$HT_6$ receptor ligands (or which are susceptible to treatment with a 5-$HT_6$ receptor ligand), i.e. they are effective for treating those medical disorders or diseases in which exerting an influence on (modulating) the 5-$HT_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-$HT_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowl Syndrome, diseases associated with neurodegeneration, such as stroke, spinal or head trauma and head injuries, such as hydrocephalus, drug addiction and obesity.

The addiction diseases include psychic disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of $5\text{-HT}_6$ receptors.

According to another aspect of the present invention, the treatment is directed, in particular, toward those disorders which can be influenced, within the sense of an expedient medicinal treatment, by the binding of preferably exogenously administered binding partners (ligands) to $5\text{-HT}_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of formula I can be used to treat a large number of signs, symptoms and/or malfunctions which are connected with the disorders of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of formula (I) are particularly suitable for treating addiction diseases caused for instance by the abuse of psychotropic substances, such as pharmaceuticals, narcotics, nicotine or alcohol, including psychic disorders and behavioral disturbances related thereto.

According to another aspect of the invention the compounds of formula (I) are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the compounds of formula I are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the present invention without limiting its scope.

EXAMPLES

I. Preparation Examples

The compounds were either characterized via $^1$H-NMR in $d_6$-dimethylsulfoxid, $CD_3OD$ or $CDCl_3$ on a 400 MHz or 500 MHz NMR instrument (Bruker AVANCE), or by mass spectrometry, generally recorded via HPLC-MS in a fast gradient on $C_{18}$-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (bs), doublet (d), broad doublet (bd), triplet (t), broad triplet (bt), quartet (q), quintet (quint.) and multiplet (m).

Example 1

Preparation of 5-azetidin-3-yl-1-(4-difluoromethoxy-benzenesulfonyl)-1H-indole, hydrochloride (compound 1)

a) Preparation of 1-(4-difluoromethoxybenzenesulfonyl)-5-iodo-1H-indole

5-Iodo-1H-indole (2.0 g, 8.23 mmol) was dissolved in dimethylformamide (DMF) (10 ml) and cooled to 0° C. Sodium hydride (494 mg, 12.34 mmol) was added in small portions. The reaction mixture was stirred for 1 hour at 0° C. 4-(Difluoro-methoxy)-benzenesulfonyl chloride (2.196 g, 9.05 mmol) was dissolved in DMF (5 ml), and added slowly to the reaction mixture. Stirring was continued for 45 minutes. Cold water (150 ml) was added to the reaction mixture. The reaction mixture was extracted twice with ethyl acetate (100 ml). The organic layer was dried over magnesium sulphate, filtered, and the solvent evaporated under reduced pressure to give a crystalline solid (3.0 g, 81%). ESI-MS [m/z]: 449.95 [M+H]$^+$. $^1$H-NMR (500 MHz, d$^6$-DMSO): δ=8.05 (d, 2H), 8.0 (s, 1H), 7.85 (d, 1H), 7.8 (d, 1H), 7.65 (d, 1H), 7.4 (t, J=70 Hz, 1H), 7.35 (d, 2H), 6.8 ppm (d, 1H).

b) Preparation of 3-[1-(4-difluoromethoxy-benzenesulfonyl)-1H-indol-5-yl]-azetidine-1-carboxylic acid tert-butyl ester In an inert atmosphere, zinc dust (300 mg, 4.59 mmol) was vigorously stirred in dimethylacetamide (1.6 ml) and heated to 65° C. Subsequently, trimethylchlorosilane (70 μl, 0.57 mmol) and dibromoethane (50 μl, 0.57 mmol) were added to the reaction mixture, and the reaction mixture was stirred for another 30 minutes at 65° C. 3-Iodo-azetidine-1-carboxylic acid tert-butyl ester (1.0 g, 3.53 mmol) in dimethylacetamide (2 ml) was added dropwise to the above prepared solution at 65° C., and then the reaction mixture was allowed to cool to room temperature. 1-(4-Difluoromethoxy-benzenesulfonyl)-5-iodo-1H-indole (961 mg, 2.12 mmol) in dimethylacetamide (4 ml) was added to the reaction mixture. Subsequently, [1,1-bis(diphenylphosphino)ferrocene]-dichloropalladium (II)-dichlormethane (52.4 mg, 0.06 mmol) and copper(I)iodide (24.4 mg, 0.13 mmol) were added. The reaction mixture was heated to 80° C. for 1 hour, before it was cooled to room temperature and quenched with water (150 ml). Ammonium chloride (2 g) was added and the reaction mixture was extracted twice with diethylether (150 ml). The organic layer was dried over magnesium sulphate, filtered, and the solvent was evaporated under reduced pressure to give an oil (950 mg). The crude product was purified by silica gel chromatography with dichloromethane as eluent, yielding the purified product (553 mg, 52%). ESI-MS [m/z]: 423.05 [M-(C$_4$H$_9$)+H]$^+$.

c) Preparation of 5-azetidin-3-yl-1-(4-difluoromethoxy-benzenesulfonyl)-1H-indole, hydrochloride 3-[1-(Difluoromethoxy-benzenesulfonyl)-1H-indol-5-yl]-azetidine-1-carboxylic acid tert-butyl ester (533 mg, 1.11 mmol) was dissolved in dichloromethane (20 ml). Trifluoroacetic acid (2 ml) was added and the reaction mixture was stirred at room temperature for 1 hour. The reaction mixture was evaporated to dryness. Ethyl acetate (50 ml) was added. The organic phase was washed with a saturated aqueous NaHCO$_3$ solution (10 ml), dried over magnesium sulphate, filtered, and evaporated to dryness to yield the crude product (420 mg, 82%).

The crude product (245 mg) was dissolved in ether (50 ml), and treated with a solution of hydrochloric acid in ether. The precipitate was collected to give the product. ESI-MS [m/z]: 379.05 [M+H]$^+$. $^1$H-NMR (500 MHz, d$^6$-DMSO): δ=9.1 (bs, 2H), 8.05 (d, 2H), 7.95 (d, 1H), 7.85 (d, 1H), 7.65 (d, 1H), 7.45 (d, 1H), 7.4 (t, J=70 Hz, 1H), 7.35 (d, 2H), 6.85 (d, 1H), 4.25 (m, 2H), 4.2 (m, 1H), 4.1 ppm (m, 2H).

Example 2

Preparation of 5-azetidin-3-yl-1-benzenesulfonyl-1H-indole, hydrochloride (compound 2)

a) Preparation of 1-benzenesulfonyl-5-iodo-1H-indole

This compound was prepared from 5-iodo-1H-indole and benzenesulfonylchloride by the method outlined under 1.a).

b) Preparation of 3-(1-benzenesulfonyl-1H-indol-5-yl)azetidine-1-carboxylic acid tert-butyl ester This compound was prepared from 1-benzenesulfonyl-5-iodo-1H-indole and 3-iodoazetidin-1-carboxylic acid tert-butyl ester by the method outlined under 1.b). ESI-MS [m/z]: 357.05 [M-($C_4H_9$)+H]$^+$.

c) Preparation of 5-azetidin-3-yl-1-benzenesulfonyl-1H-indole, hydrochloride This compound was prepared from 3-(1-benzenesulfonyl-1H-indol-5-yl)-azetidine-1-carboxylic acid tert-butyl ester by the method outlined under 1.c). ESI-MS [m/z]: 313.05 [M+H]$^+$. $^1$H-NMR (500 MHz, d$^6$-DMSO): δ=9.4 (bs, 1H), 9.1 (bs, 1H), 8.0 (d, 2H), 7.95 (d, 1H), 7.85 (d, 1H), 7.7 (m, 2H), 7.6 (m, 2H), 7.4 (d, 1H), 6.85 (d, 1H), 4.25 (m, 2H), 4.15 (m, 1H), 4.05 ppm (m, 2H).

Example 3

Preparation of 5-azetidin-3-yl-1-(4-oxazol-5-yl-benzenesulfonyl)-1H-indole, hydrochloride (compound 3)

a) Preparation of 5-iodo-1-(4-oxazol-5-yl-benzenesulfonyl)-1H-indole

This compound was prepared from 5-iodo-1H-indole and 4-oxazol-5-ylbenzene-sulfonyl-chloride by the method outlined under 1.a).

b) Preparation of 3-[1-(4-oxazol-5-yl-benzenesulfonyl)-1H-indol-5-yl]-azetidine 1-carboxylic acid tert-butyl ester This compound was prepared from 5-Iodo-1-(4-oxazol-5-yl-benzenesulfonyl)-1H-indole and 3-iodoazetidin-1-carboxylic acid tert-butyl ester by the method outlined under 1.b). ESI-MS [m/z]: 380.05 [M-Boc-+H]$^+$.

c) Preparation of 5-azetidin-3-yl-1-(4-oxazol-5-yl-benzenesulfonyl)-1H-indole This compound was prepared from 3-[1-(4-oxazol-5-yl-benzenesulfonyl)-1H-indol-5-yl]-azetidine-1-carboxylic acid tert-butyl ester by the method outlined under 1.c). ESI-MS [m/z]: 380.05 [M+H]$^+$. $^1$H-NMR (500 MHz, d$^6$-DMSO): δ=8.75 (bs, 1H), 8.55 (s, 1H), 8.1 (d, 2H), 7.95 (d, 1H), 7.9 (m, 4H), 7.65 (s, 1H), 7.4 (d, 1H), 6.85 (d, 1H), 4.25 (m, 2H), 4.2 (m, 1H), 4.1 ppm (m, 2H).

Example 4

Preparation of 1-(4-Difluoromethoxy-benzenesulfonyl)-5-(1-propyl-azetidin-3-yl)-1H-indole, hydrochloride (compound 4)

5-Azetidin-3-yl-1-(difluoromethoxy-benzensulfonyl)-1H-indole (100 mg, 0.24 mmol) and propionaldehyde (30 μl, 0.34 mmol) were dissolved in tetrahydrofurane (THF) (10 ml). Acetic acid (26 μl, 0.51 mmol) and sodium trisacetoxyborohydride (145 mg, 0.69 mmol) were sequentially added, and the reaction mixture was stirred for 10 minutes. The reaction mixture was concentrated and the residue dissolved in $H_2O$ (20 ml) and diethyl ether (50 ml). The organic phase was dried over magnesium sulphate, filtered, and evaporated to dryness. The crude product was purified by silica gel chromatography with dichloromethane/methanol (90:10) as eluent, yielding the purified product, which was subsequently converted into the hydrochloride (41 mg, 37%). ESI-MS [m/z]: 421.10 [M+H]$^+$. $^1$H-NMR (400 MHz, d$^6$-DMSO): δ=10.75 (bs, 1H), 8.05 (d, 2H), 7.95 (d, 1H), 7.85 (d, 1H), 7.7 (s, 1H), 7.45 (bs, 1H), 7.4 (t, J=70 Hz, 1H), 7.35 (d, 2H), 6.85 (d, 1H), 4.4-4.1 (m, 5H), 3.15 (bs, 2H), 1.55 (m, 2H), 0.95 ppm (t, 3H).

Example 5

Preparation of 1-benzenesulfonyl-5-(1-propylazetidin-3-yl)-1H-indole, hydrochloride (compound 5)

This compound was prepared from 5-azetidin-3-yl-1-(benzensulfonyl)-1H-indole by the method outlined for compound 4. ESI-MS [m/z]: 355.15 [M+H]$^+$. $^1$H-NMR (500 MHz, d$^6$-DMSO): δ=10.8 (bs, 1H), 7.95 (d, 2H), 7.9 (d, 1H), 7.85 (d, 1H), 7.7 (d, 2H), 7.6 (m, 2H), 7.4 (m, 1H), 6.85 (d, 1H), 4.4 (bs, 2H), 4.3 (bs, 1H), 4.1 (bs, 2H), 3.15 (bs, 2H), 1.55 (m, 2H), 0.95 ppm (t, 3H).

Example 6

Preparation of 1-(4-oxazol-5-yl-benzenesulfonyl)-5-(1-propylazetidin-3-yl)-1H-indole, hydrochloride (compound 6)

This compound was prepared from 5-azetidin-3-yl-1-(4-oxazol-5-yl-benzensulfonyl)-1H-indole by the method outlined for compound 4. ESI-MS [m/z]: 422.15 [M+H]$^+$. $^1$H-NMR (500 MHz, d$^6$-DMSO): δ=10.75 (bs, 1H), 8.55 (s, 1H), 8.1 (d, 2H), 7.9 (m, 5H), 7.7 (s, 1H), 7.4 (m, 1H), 6.85 (d, 1H), 4.4 (m, 2H), 4.25 (m, 1H), 4.1 (m, 2H), 3.15 (m, 2H), 1.55 (m, 2H), 0.95 ppm (t, 3H).

Example 7

Preparation of 5-azetidin-3-yl-1-benzenesulfonyl-2,3-dihydro-1H-indole, hydrochloride (compound 7)

5-Azetidin-3-yl-1-benzensulfonyl-1H-indole (150 mg, 0.48 mmol) was dissolved in methanol (10 ml) and 3 times run through an H-Cube (5% Pd/C cartridge) with a flow rate of 0.5 ml/minute at 50° C. at 10 bar. The reaction mixture was concentrated and the residue was purified by HPLC chromatography with water/0.1% trifluoroacetic acid and acetonitrile/0.1% trifluoroacetic acid. The residue was converted into the hydrochloride to yield the product (26 mg, 15%). ESI-MS [m/z]: 315.15 [M+H]$^+$. $^1$H-NMR (400 MHz, d$^6$-DMSO): δ=9.15 (bs, 1H), 8.8 (bs, 1H), 7.85 (d, 2H), 7.7 (t, 1H), 7.6 (m, 2H), 7.45 (d, 1H), 7.25 (s, 1H), 7.2 (d, 1H), 4.2 (m, 2H), 4.1-3.9 (m, 5H), 2.95 ppm (t, 3H).

Example 8

Preparation of 5-azetidin-3-yl-1-(4-oxazol-5-yl-benzenesulfonyl)-2,3-dihydro-1H-indole, (compound 8)

This compound was prepared from 5-azetidin-3-yl-1-(4-oxazol-5-yl-benzensulfonyl)-1H-indole by the method outlined for compound 7. ESI-MS [m/z]: 382.05 [M+H]$^+$. $^1$H-NMR (400 MHz, d$^6$-DMSO): δ=8.7 (bs, 1H), 8.55 (s, 1H), 7.9 (m, 5H), 7.45 (d, 1H), 7.25 (s, 1H), 7.2 (d, 1H), 4.2 (m, 2H), 4.1-3.9 (m, 5H), 2.95 ppm (t, 3H).

Example 8a 5-azetidin-3-yl-1-(4-oxazol-5-yl-benzenesulfonyl)-2,3-dihydro-1H-indole, hydrochloride (compound 8a)

Example 9

Preparation of 1-Benzenesulfonyl-5-(1-propyl-azetidin-3-yl)-2,3-dihydro-1H-indole hydrochloride (compound 9)

1-Benzenesulfonyl-5-(1-propyl-azetidin-3-yl)-1H-indole, (50 mg, 0.13 mmol) was dissolved in methanol (20 ml) and run through an H-Cube (5% Pd/C cartridge) with a flow rate of 0.5 ml/minute at 50° C. at 10 bar. The reaction mixture was concentrated in vacuo. To the residue was added acetonitrile and water and the solution was lyophilised to give the product (38 mg, 76%). ESI-MS [m/z]: 357.15 [M+H]$^+$. $^1$H-NMR (400 MHz, d$^6$-DMSO): δ=10.35 (bs, 1H), 7.85 (d, 2H), 7.7 (t, 1H), 7.6 (t, 2H), 7.45 (d, 1H), 7.3 (s, 1H), 7.2 (d, 1H), 4.35 (m, 1H), 4.2 (m, 1H), 4.05-3.9 (m, 5H), 3.15 (m, 2H), 2.95 (t, 3H), 1.5 (m, 2H), 0.9 (t, 3H).

Example 9a

1-Benzenesulfonyl-5-(1-propyl-azetidin-3-yl)-2,3-dihydro-1H-indole (compound 9a)

Example 10

Preparation of 1-(4-oxazol-5-yl-benzenesulfonyl)-5-(1-propyl-azetidin-3-yl)-2,3-dihydro-1H-indole hydrochloride (compound 10)

This compound was prepared from 1-(4-oxazol-5-yl-benzensulfonyl)-5-(1-propyl-azetidin-3-yl)-1H-indole by the method outlined for compound 9. ESI-MS [m/z]: 424.15 [M+H]$^+$.

Example 10a

Preparation of 1-(4-oxazol-5-yl-benzenesulfonyl)-5-(1-propyl-azetidin-3-yl)-2,3-dihydro-1H-indole (compound 10a)

Example 11

Preparation of 3-[1-(4-isopropyl-benzenesulfonyl)-1H-indol-5-yl]-azetidine-1-carboxylic acid tert-butyl ester (compound 11)

a) Preparation of 5-iodo-1-triisopropylsilanyl-1H-indole

5-Iodo-1H-indole (5.0 g, 20.57 mmol) was dissolved in CH$_2$Cl$_2$ (50 ml) and DMF (1 ml) and cooled to 0° C. Sodium hydride (1.234 g, 30.86 mmol) was added in small portions, and the reaction mixture was stirred for 30 minutes at 0° C. Triisopropylchlorosilane (4.54 ml, 20.57 mmol) was added slowly to the reaction mixture, and stirring was continued for 1 hour. Cold water (200 ml) was added to the reaction mixture, which was extracted twice with ethyl acetate (100 ml). The organic layer was dried over magnesium sulphate, filtered, and the solvent was evaporated under reduced pressure to give an oil (8.8 g, 99%).

b) Preparation of 3-(1-triisopropylsilanyl-1H-indol-5-yl)-azetidine-1-carboxylic acid tert-butyl ester In an inert atmosphere, zinc dust (300 mg, 4.59 mmol) was vigorously stirred in dimethylacetamide (1.6 ml) and heated to 65° C. Subsequently, trichloromethylsilane (70 µl, 0.57 mmol) and dibromoethane (50 µl, 0.57 mmol) were added, and the reaction mixture was stirred for another 30 minutes at 65° C. 3-Iodo-azetidine-1-carboxylic acid tert-butyl ester (1.0 g, 3.53 mmol) in dimethylacetamide (2 ml) was added dropwise to the above prepared solution at 65° C., and then the reaction mixture was allowed to cool to room temperature. 5-Iodo-1-triisopropylsilanyl-1H-indole (855 mg, 1.98 mmol) in dimethylacetamide (4 ml) was added to the reaction mixture. Subsequently, [1,1-bis(diphenylphosphino)ferrocene] dichloropalladium(II)-dichlormethane (52.4 mg, 0.06 mmol) and copper(I)iodide (24.4 mg, 0.13 mmol) were added. The reaction mixture was heated to 80° C. for 2 hours, cooled to room temperature and quenched with water (150 ml). Ammonium chloride (2 g) was added, and the reaction mixture was extracted twice with diethylether (150 ml). The organic layer was dried over magnesium sulphate, filtered, and the solvent was evaporated under reduced pressure to give an oil (1.1 g, 64% purity).

c) Preparation of 3-(1H-indol-5-yl)-azetidine-1-carboxylic acid tert-butyl ester 3-(1-Triisopropylsilanyl-1H-indol-5-yl)-azetidine-1-carboxylic acid tert-butyl ester (1.1 g, 64% purity, 1.63 mmol) was dissolved in THF (20 ml). Tetrabutylammonium fluoride (3.25 ml, 1 molar solution in THF) was added and the reaction mixture was stirred for 5 minutes at room temperature. The reaction mixture was concentrated, and the residue was dissolved in H$_2$O (50 ml) and diethyl ether (50 ml). The crude product was purified by silica gel chromatography with dichloromethane as eluent, yielding the purified product (275 mg, 51% for 2 steps).

d) Preparation of 3-[1-(4-isopropyl-benzenesulfonyl)-1H-indol-5-yl]-azetidine-1-carboxylic acid tert-butyl ester 3-(1H-Indol-5-yl)-azetidine-1-carboxylic acid tert-butyl ester (135 mg, 0.5 mmol) was dissolved in DMF (10 ml) and cooled to 0° C. Sodium hydride (35.7 mg, 0.74 mmol) was added, and the reaction mixture was stirred for 1 hour at 0° C. 4-Isopropyl-benzenesulfonyl chloride (98 µl, 0.55 mmol) was added slowly to the reaction mixture. Stirring was continued for 10 minutes. Cold water (100 ml) was added to the reaction mixture, and it was extracted twice with diethyl ether (80 ml). The organic layer was dried over magnesium sulphate, filtered, and the solvent was evaporated under reduced pressure to give a crystalline solid (75 mg, 33%). ESI-MS [m/z]: 355.15 [M-(Boc)+H]$^+$.

Examples 12 to 18

Those compounds have been prepared from 3-(1H-Indol-5-yl)-azetidine-1-carb-oxylic acid tert-butyl ester and a suitable sulfonylchloride compound by the method outlined for compound 11.

Example 12

3-[1-(4-Oxazol-5-ylbenzenesulfonyl)-1H-indol-5-yl]-azetidine-1-carboxylic acid tert-butyl ester (compound 12)

Example 13

3-[1-(3-Trifluoromethylbenzenesulfonyl)-1H-indol-5-yl]-azetidine-1-carboxylic acid tert-butyl ester (compound 13)

ESI-MS [m/z]: 425.15 [M-(C$_4$H$_9$)+H]$^+$.

Example 14

3-[1-(3-Trifluoromethoxybenzenesulfonyl)-1H-indol-5-yl]-azetidine-1-carboxylic acid tert-butyl ester (compound 14)

ESI-MS [m/z]: 441.15 [M-(C$_4$H$_9$)+H]$^+$.

Example 15

3-[1-(3-Difluoromethoxybenzenesulfonyl)-1H-indol-5-yl]-azetidine-1-carboxylic acid tert-butyl ester (compound 15)

ESI-MS [m/z]: 423.15 [M-(C$_4$H$_9$)+H]$^+$.

Example 16

3-[1-(2-Trifluoromethylbenzenesulfonyl)-1H-indol-5-yl]-azetidine-1-carboxylic acid tert-butyl ester (compound 16)

ESI-MS [m/z]: 425.40 [M-(C$_4$H$_9$)+H]$^+$

Example 17

3-[1-(2-Trifluoromethoxybenzenesulfonyl)-1H-indol-5-yl]-azetidine-1-carboxylic acid tert-butyl ester (compound 17)

ESI-MS [m/z]: 441.40 [M-(C$_4$H$_9$)+H]$^+$.

Example 18

3-[1-(Pyridine-3-sulfonyl)-1H-indol-5-yl]-azetidine-1-carboxylic acid tert-butyl ester (compound 18)

ESI-MS [m/z]: 358.35 [M-(C$_4$H$_9$)+H]$^+$.

Example 19

Preparation of 5-azetidin-3-yl-1-(3-trifluoromethyl-benzenesulfonyl)-1H-indole, hydrochloride (compound 19)

3-[1-(3-Trifluoromethyl-benzenesulfonyl)-1H-indol-5-yl]-azetidine-1-carboxylic acid tert-butyl ester (compound 13) (400 mg, 0.83 mmol) was dissolved in formic acid (4.7 ml) at 0° C. and stirred for 2 hours. The reaction mixture was evaporated to dryness at 30° C. The residue was dissolved in ethyl acetate (50 ml), and washed with a 1 molar aqueous solution of NaOH (10 ml). The organic layer was dried over magnesium sulphate, filtered, and evaporated to dryness to yield the crude product (231 mg, 82%). The crude product was dissolved in ether (50 ml), treated with a solution of hydrochloric acid in ether, and the precipitate was collected to give the product (151 mg, 44%).

ESI-MS [m/z]: 381.15 [M+H]$^+$. $^1$H-NMR (400 MHz, d$^6$-DMSO): δ=9.0 (bs, 2H), 8.3 (m, 2H), 8.1 (d, 1H), 8.0 (d, 1H), 7.95 (d, 1H), 7.85 (t, 1H), 7.7 (s, 1H), 7.45 (d, 1H), 6.9 (d, 1H), 4.25 (m, 2H), 4.2 (m, 1H), 4.05 ppm (m, 2H).

Examples 20 to 24

Those compounds have been prepared from the corresponding compounds 14 to 18 by the method outlined for compound 19.

Example 20

5-Azetidin-3-yl-1-(3-trifluoromethoxybenzenesulfonyl)-1H-indole, hydrochloride (compound 20)

ESI-MS [m/z]: 397.15 [M+H]$^+$. $^1$H-NMR (400 MHz, d$^6$-DMSO): δ=9.0 (bs, 2H), 8.05-7.95 (m, 3H), 7.9 (d, 1H), 7.75 (d, 2H), 7.7 (s, 1H), 7.4 (d, 1H), 6.9 (d, 1H), 4.25 (m, 2H), 4.2 (m, 1H), 4.1 ppm (m, 2H).

Example 21

5-Azetidin-3-yl-1-(3-difluoromethoxybenzenesulfonyl)-1H-indole, hydrochloride (compound 21)

ESI-MS [m/z]: 379.15 [M+H]$^+$. $^1$H-NMR (400 MHz, d$^6$-DMSO): δ=9.05 (bs, 2H), 7.95 (d, 1H), 7.9 (d, 1H), 7.85

(d, 1H), 7.8 (s, 1H), 7.65 (m, 2H), 7.55 (d, 1H), 7.4 (d, 1H), 7.35 (t, J=70 Hz, 1H), 6.9 (d, 1H), 4.25 (m, 2H), 4.2 (m, 1H), 4.1 ppm (m, 2H).

Example 22

5-Azetidin-3-yl-1-(2-trifluoromethylbenzenesulfonyl)-1H-indole (compound 22)

ESI-MS [m/z]: 381.40 [M+H]$^+$. $^1$H-NMR (400 MHz, d$^6$-DMSO): δ=8.60 (bs, 1H), 8.10 (d, 1H), 7.95 (t, 1H), 7.85 (m, 2H), 7.75 (m, 2H), 7.60 (d, 1H), 7.45 (d, 1H), 6.95 (d, 1H), 4.30-4.15 (m, 3H), 4.1 ppm (m, 2H).

Example 22a

5-Azetidin-3-yl-1-(2-trifluoromethylbenzenesulfonyl)-1H-indole hydrochloride (compound 22a)

Example 23

5-Azetidin-3-yl-1-(2-trifluoromethoxybenzenesulfonyl)-1H-indole (compound 23)

ESI-MS [m/z]: 397.40 [M+H]$^+$. $^1$H-NMR (400 MHz, d$^6$-DMSO): δ=8.60 (bs, 1H), 8.30 (d, 1H), 7.90 (t, 1H), 7.75-7.65 (m, 4H), 7.60 (d, 1H), 7.35 (d, 1H), 6.90 (d, 1H), 4.30-4.15 (m, 3H), 4.1 ppm (m, 2H).

Example 23a

5-Azetidin-3-yl-1-(2-trifluoromethoxybenzenesulfonyl)-1H-indole, hydrochloride (compound 23a)

Example 24

Azetidin-3-yl-1-(pyridine-3-sulfonyl)-1H-indole, hydrochloride (compound 24)

ESI-MS [m/z]: 314.10 [M+H]$^+$. $^1$H-NMR (400 MHz, d$^6$-DMSO): δ=9.40 (bs, 1H), 9.2 (s, 1H), 9.1 (bs, 1H), 8.85 (d, 1H), 8.40 (d, 1H), 8.05 (d, 1H), 7.90 (d, 1H), 7.70 (s, 1H), 7.65 (m, 1H), 7.45 (d, 1H), 6.90 (d, 1H), 4.30-4.15 (m, 3H), 4.1 ppm (m, 2H).

Example 25

Preparation of 5-(1-propyl-azetidin-3-yl)-1-(3-trifluoromethylbenzenesulfonyl)-1H-indole, hydrochloride (compound 25)

5-Azetidin-3-yl-1-(3-trifluoromethyl-benzensulfonyl)-1H-indole (compound 22) (70 mg, 0.17 mmol), acetic acid (13 μl, 0.25 mmol) and sodium trisacetoxyborohydride (53.4 mg, 0.25 mmol) were dissolved in THF (10 ml) at 0° C. Propionaldehyde (21 μl, 0.29 mmol) was dissolved in THF (1 ml), and slowly added to the reaction mixture. After 5 minutes, the reaction mixture was concentrated, and the residue was dissolved in a saturated aqueous solution of NaHCO$_3$ and ethyl acetate. The organic layer was dried over magnesium sulphate, filtered, and a solution of hydrochloric acid in diethyl ether (1 ml) was added. The solution was evaporated to dryness. Diethyl ether (50 ml) was added, and the mixture was stirred overnight. The precipitate was filtered off, and dried to give a white solid (48 mg, 62%). ESI-MS [m/z]: 423.15 [M+H]$^+$. $^1$H-NMR (400 MHz, d$^6$-DMSO): δ=10.85 (bs, 1H), 8.35 (m, 2H), 8.15 (d, 1H), 8.0 (m, 2H), 7.85 (t, 1H), 7.7 (s, 1H), 7.45 (m, 1H), 6.9 (d, 1H), 4.25 (m, 2H), 4.4-4.1 (m, 5H), 3.15 (bs, 2H), 1.55 (m, 2H), 0.95 ppm (t, 3H).

Example 26

5-(1-Propylazetidin-3-yl)-1-(3-trifluoromethoxybenzenesulfonyl)-1H-indole, hydrochloride (compound 26)

This compound was prepared from compound 20 by the experimental procedure outlined for the example 25. ESI-MS [m/z]: 439.15 [M+H]$^+$. $^1$H-NMR (400 MHz, d$^6$-DMSO): δ=10.85 (bs, 1H), 8.05 (m, 2H), 7.95 (d, 1H), 7.9 (d, 1H), 7.75 (m, 2H), 7.7 (s, 1H), 7.45 (m, 1H), 6.9 (d, 1H), 4.4 (bs, 2H), 4.3 (bs, 1H), 4.1 (bs, 2H), 3.15 (bs, 2H), 1.55 (m, 2H), 0.9 ppm (t, 3H).

Example 27

5-(1-Propylazetidin-3-yl)-1-(3-difluoromethoxybenzenesulfonyl)-1H-indole, hydrochloride (compound 27)

This compound was prepared from compound 21 by the experimental procedure outlined for the example 25. ESI-MS [m/z]: 421.15 [M+H]$^+$. $^1$H-NMR (400 MHz, d$^6$-DMSO): δ=10.7 (bs, 1H), 7.95 (d, 1H), 7.9 (d, 1H), 7.85 (d, 1H), 7.8 (s, 1H), 7.7 (s, 1H), 7.65 (t, 1H), 7.55 (s, 1H), 7.4 (d, 1H), 7.35 (t, J=70 Hz, 1H), 6.9 (d, 1H), 4.4 (bs, 2H), 4.15 (bs, 3H), 3.15 (bs, 2H), 1.55 (m, 2H), 0.9 ppm (t, 3H).

Examples 28 to 43

Those compounds have been prepared by the methods outlined above.

Example 28

5-(1-Ethylazetidin-3-yl)-1-benzenesulfonyl-1H-indole, hydrochloride (compound 28)

Example 29

5-(1-Methylazetidin-3-yl)-1-benzenesulfonyl-1H-indole, hydrochloride (compound 29)

Example 30

5-Azetidin-3-yl-1-(3-trifluoromethyl-benzenesulfonyl)-2,3-dihydro-1H-indole, hydrochloride (compound 30)

ESI-MS [m/z]: 383.1 [M+H]$^+$. $^1$H-NMR (500 MHz, d$_4$-methanol): δ=8.1 (d, 1H), 8.0 (s, 1H), 7.95 (d, 1H), 7.8 (t, 1H), 7.65 (d, 1H), 7.3 (d, 1H), 7.25 (s, 1H), 4.4 (m, 2H), 4.25 (m, 3H), 4.0 (t, 2H), 2.95 ppm (t, 2H).

Example 31

5-Azetidin-3-yl-1-benzenesulfonyl-3-chloro-1H-indole, hydrochloride (compound 31)

a) Preparation of 3-(1-Benzenesulfonyl-3-chloro-1H-indol-5-yl)-azetidine-1-carboxylic acid tert-butyl ester 3-(1-Benzenesulfonyl-1H-indol-5-yl)-azetidine-1-carboxylic acid tert-butyl ester (1333 mg, 3.23 mmol) and 1-chloropyrrolidine-2,5-dione (484 mg, 3.55 mmol) were dissolved in acetonitril (10 ml). The reaction mixture was stirred at 100° C. in a microwave unit for 1 hour. The volatile compounds were evaporated under reduced pressure, the residue was absorbed on Celite and subsequently purified by silica gel chromatography with cyclohexane and ethylacetate (0 to 30%) as eluent, yielding the purified product (894 mg, 56% yield).

ESI-MS [m/z]: 391.1 [M+H-tBu]$^+$.

b) Preparation of 5-Azetidin-3-yl-1-benzenesulfonyl)-3-chloro-1H-indole, hydrochloride 3-(1-Benzenesulfonyl-3-chloro-1H-indol-5-yl)-azetidine-1-carboxylic acid tert-butyl ester (894 mg, 2.0 mmol) was dissolved in formic acid (5 ml) at 0° C. The reaction mixture was stirred at room temperature for 5 hours. Subsequently volatile compounds were evaporated under reduced pressure to give a white solid. To the residue was added acetonitrile and hydrochloride acid (0.1 molar solution) and the solution was lyophilised to give the product (552 mg, 68%).

ESI-MS [m/z]: 347.1 [M+H]$^+$. $^1$H-NMR (500 MHz, d$_6$-DMSO): δ=9.25 (bs, 1H), 8.9 (bs, 1H), 8.2 (s, 1H), 8.05 (m, 3H), 7.75 (t, 1), 7.65 (m, 3H), 7.55 (d, 1H), 4.25 (m, 3H), 4.1 ppm (m, 2H).

Example 32

Preparation of 4-(5-(5-(azetidin-3-yl)-1H-indazol-1-ylsulfonyl)-2-fluorophenyl)oxazole, formic acid salt (compound 32)

a) Preparation of tert-butyl 3-(1-(4-fluoro-3-(oxazol-4-yl)phenylsulfonyl)-1H-indazol-5-yl)azetidine-1-carboxylate This compound was prepared from tert-butyl 3-(1H-indazol-5-yl)azetidine-1-carboxylate and 4-fluoro-3-(oxazol-4-yl)benzene-1-sulfonyl chloride by analogy to the method outlined in example 44.c, below).

ESI-MS [m/z]: 499.1 [M+H]$^+$.

b) Preparation of 4-(5-(5-(azetidin-3-yl)-1H-indazol-1-ylsulfonyl)-2-fluorophenyl)oxazole, formic acid salt This compound was prepared from tert-butyl 3-(1-(4-fluoro-3-(oxazol-4-yl)phenylsulfonyl)-1H-indazol-5-yl)azetidine-1-carboxylate by analogy to the method outlined in example 44.d below).

ESI-MS [m/z]: 399.1 [M+H]$^+$.

Example 33

5-(Azetidin-3-yl)-1-(naphthalene-2-sulfonyl)-1H-indole, hydrochloride (compound 33)

ESI-MS [m/z]: 363.1 [M+H]$^+$. $^1$H-NMR (500 MHz, d$_4$-MeOD): δ=8.65 (bs, 1H), 8.1 (d, 1H); 8.05 (d, 1H), 7.95 (d, 1H), 7.9 (d, 1H), 7.8 (d, 1H); 7.75 (m, 1H), 7.7-7.6 (m, 3H), 7.4 (m, 1H), 6.8 (d, 1H), 4.4-4.25 ppm (m, 5H).

Example 34

5-(Azetidin-3-yl)-1-(2-fluoro-benzenesulfonyl)-1H-indole, hydrochloride (compound 34)

ESI-MS [m/z]: 331.0 [M+H]$^+$. $^1$H-NMR (500 MHz, d$_4$-MeOD): δ=8.15 (m, 1H), 7.9 (d, 1H), 7.75-7.70 (m, 2H), 7.65 (bs, 1H), 7.45 (m, 1H), 7.35 (m, 1H), 7.25 (m, 1H), 6.8 (d, 1H), 4.45-4.35 (m, 3H), 4.30 ppm (m, 2H).

Example 35

5-(Azetidin-3-yl)-1-(3-phenoxy-benzenesulfonyl)-1H-indole, hydrochloride (compound 35)

ESI-MS [m/z]: 405.1 [M+H]$^+$. $^1$H-NMR 500 MHz, d$_4$-MeOD): δ=7.95 (d, 1H), 7.7-7.65 (m, 3H), 7.5 (t, 1H), 7.45-7.35 (m, 4H), 7.25 (m, 1H), 7.2 (m, 1H), 6.95 (d, 2H), 6.8 (d, 1H), 4.5-4.3 ppm (m, 5H).

Example 36

5-(Azetidin-3-yl)-1-(3-chloro-benzenesulfonyl)-1H-indole, hydrochloride (compound 36)

ESI-MS [m/z]: 347.0 [M+H]$^+$. $^1$H-NMR (500 MHz, d$_4$-MeOD): δ=8.05 (d, 1H), 7.95 (m, 1H), 7.9 (m, 1H), 7.75 (d, 1H), 7.7-7.65 (m, 2H), 7.55 (t, 1H), 7.45 (m, 1H), 6.85 (d, 1H), 4.5-4.3 ppm (m, 5H).

Example 37

5-(Azetidin-3-yl)-1-(3-fluoro-benzenesulfonyl)-1H-indole, hydrochloride (compound 37)

ESI-MS [m/z]: 331.0 [M+H]$^+$. $^1$H-NMR (400 MHz, d$_4$-MeOD): δ=8.05 (d, 1H), 7.8 (m, 1H), 7.75 (d, 1H), 7.7 (m, 1H), 7.65 (bs, 1H), 7.6 (m, 1H), 7.4 (m, 2H), 6.85 (d, 1H), 4.45-4.3 ppm (m, 5H).

Example 38

5-(Azetidin-3-yl)-1-(3-trifluoromethyl-benzenesulfonyl)-2,3-dihydro-1H-indole, hydrochloride (compound 38)

ESI-MS [m/z]: 383.0 [M+H]$^+$. $^1$H-NMR (500 MHz, d$_4$-MeOD): δ=8.15 (d, 1H), 8.05 (s, 1H); 8.0 (d, 1H), 7.8 (t, 1H), 7.65 (d, 1H), 7.3 (d, 1H), 7.27 (s, 1H), 4.4 (m, 2H), 4.25 (m, 3H), 4.05 (t, 2H), 2.95 ppm (t, 2H).

Example 39

5-(Azetidin-3-yl)-1-(4-fluoro-benzenesulfonyl)-1H-indole, hydrochloride (compound 39)

ESI-MS [m/z]: 331.1 [M+H]$^+$. $^1$H-NMR (500 MHz, d$_4$-MeOD): δ=8.1-8.05 (m, 3H), 7.75 (d, 1H), 7.7 (s, 1H), 7.4 (m, 1H), 7.3 (m, 2H), 6.85 (d, 1H), 4.5-4.3 ppm (m, 5H).

Example 40

5-(Azetidin-3-yl)-1-(1-biphenyl-2-sulfonyl)-1H-indole, hydrochloride (compound 40)

ESI-MS [m/z]: 389.1 [M+H]$^+$. $^1$H-NMR (500 MHz, d$_4$-MeOD): δ=8.3 (m, 1H), 7.75 (m, 1H), 7.7 (m, 1H), 7.6 (bs,

1H), 7.5 (d, 1H), 7.4 (m, 1H), 7.35-7.3 (m, 3H), 7.25 (m, 1H), 7.0 (m, 2H), 6.75 (d, 1H), 6.4 (d, 1H), 4.45 (m, 2H), 4.4-4.3 ppm (m, 3H).

Example 41

5-(Azetidin-3-yl)-1-(naphthalene-1-sulfonyl)-1H-indole, hydrochloride (compound 41)

ESI-MS [m/z]: 363.1 [M+H]$^+$. $^1$H-NMR (500 MHz, d$_6$-DMSO): δ=9.55 (bs, 1H), 9.2 (bs, 1H), 8.6 (d, 1H), 8.45 (d, 1H), 8.3 (d, 1H), 8.1 (d, 1H), 8.05 (d, 1H), 7.7 (m, 3H), 7.65 (m, 2H), 7.3 (d, 1H), 6.8 (d, 1H), 4.2 (m, 2H), 4.1 (m, 1H), 4.0 ppm (m, 2H).

Example 42

5-(Azetidin-3-yl)-1-(3-trifluoromethoxy-benzenesulfonyl)-2,3-dihydro-1H-indole, hydrochloride (compound 42)

ESI-MS [m/z]: 399.0 [M+H]$^+$. $^1$H-NMR (500 MHz, d$_4$-MeOD): δ=7.85 (m, 1H), 7.7-7.6 (m, 4H), 7.3 (d, 1H), 7.25 (s, 1H), 4.4 (m, 2H), 4.25 (m, 3H), 4.05 (t, 2H), 3.0 ppm (t, 2H).

Example 43

5-(Azetidin-3-yl)-1-(3-difluoromethoxy-benzenesulfonyl)-2,3-dihydro-1H-indole, hydrochloride (compound 43)

ESI-MS [m/z]: 381.1 [M+H]$^+$. $^1$H-NMR (500 MHz, d$_4$-MeOD): δ=7.7 (d, 1H), 7.65-7.6 (m, 2H), 7.55 (s, 1H), 7.45 (d, 1H), 7.3 (d, 1H), 7.25 (s, 1H), 6.9 (t, 1H), 4.4 (m, 2H), 4.25 (3H), 4.0 (t, 2H), 3.0 ppm (t, 2H).

Example 44

Preparation of 5-(azetidin-3-yl)-1-(3-(difluoromethoxy)phenylsulfonyl)-1H-indazole, formic acid salt (compound 44)

a) Preparation of 5-iodo-1H-indazole

5-Bromo-1H-indazole (2.0 g, 10.15 mmol) was dissolved in dioxane (50 ml) and stirred under N$_2$ atmosphere. Copper iodide (97 mg, 0.51 mmol), sodium iodide (3.04 g, 20.3 mmol) and trans-1,2-bis-(methylamino)-cyclohexane (147 mg, 1.02 mmol) was added and the reaction mixture was stirred for 68 hours at 110° C. The cooled solution was filtered and the filtrate concentrated under reduced pressure. The residue was dissolved in DCM (20 mL) and extracted with aqueous ammonia (1M, 5×10 mL). The organic phase was then washed three times with an aqueous Na$_2$S$_2$O$_3$ solution, dried over MgSO$_4$, filtered and concentrated under reduced pressure to give the product as a white solid (2.43 g, 100%).
ESI-MS [m/z]: 244.9 [ M+H]$^+$.

b) Preparation of tert-butyl 3-(1H-indazol-5-yl)azetidine-1-carboxylate (1-(tert-Butoxycarbonyl)azetidin-3-yl)zinc(II) iodide was prepared as previously described. 5-Iodo-1H-indazole (1.82 g, 7.46 mmol) in dimethylacetamide (DMA, 19 ml) was added to a solution of (1-(tert-butoxycarbonyl)azetidin-3-yl) zinc(II) iodide (18.64 mmol) in 18.6 mL DMA. Subsequently, [1,1-bis(diphenylphosphino)ferrocene]dichloropalladium(II)-dichlormethane (183 mg, 0.22 mmol) and copper (I)iodide (170 mg, 0.89 mmol) were added. The reaction mixture was heated to 80° C. for 12 hours, before it was cooled to room temperature and quenched with water (40 ml) and MTBE (40 mL). Ammonium chloride (1M) was added. After separation of the layers the organic layer was dried over MgSO$_4$, filtered, and the solvent was evaporated under reduced pressure to give an oil (3 g). The crude product was purified by silica gel chromatography with dichloromethane as eluent, yielding the purified product (1.20 g, 59%).
ESI-MS [m/z]: 274.1 [M-(C$_4$H$_9$)+H]$^+$.

c) Preparation of tert-butyl 3-(1-(3-(difluoromethoxy)phenylsulfonyl)-1H-indazol-5-yl)azetidine-1-carboxylate tert-Butyl-3-(1H-indazol-5-yl)azetidine-1-carboxylate (200 mg, 0.73 mmol) was dissolved in pyridine (3 ml) and 4-difluoromethoxybenzenesulfonyl chloride (192 mg, 0.77 mmol) was added at 0° C. After stirring at ambient temperature for 60 h, the reaction mixture was diluted with EtOAc and washed with water. The organic layer was dried over Na$_2$SO$_4$, filtered and volatile compounds were evaporated under reduced pressure. The residue was purified by column chromatography on silica gel (CH$_2$Cl$_2$:methanol, 95:5) to afford the title compound (172 mg, 49%) as a white amorphous solid.
ESI-MS [m/z]: 480.1 [M+H]$^+$. $^1$H-NMR (400 MHz, d$^6$-DMSO): δ=8.6 (s, 2H), 8.1 (d, 1H), 7.8 (s, 1H), 7.8 (d, 1H), 7.65 (m, 2H), 7.55 (m, 1H), 4.3 (m, 2H), 3.95 (m, 1H), 3.85 (m, 2H), 1.4 (s, 9H).

d) Preparation of 5-(azetidin-3-yl)-1-(3-(difluoromethoxy)phenylsulfonyl)-1H-indazole, formic acid salt tert-Butyl 3-(1-(3-(difluoromethoxy)phenylsulfonyl)-1H-indazol-5-yl)azetidine-1-carboxylate (154 mg, 0.32 mmol) was dissolved in formic acid (2 ml) at 0° C. The reaction mixture was stirred at room temperature for 16 hours. Subsequently volatile compounds were evaporated under reduced pressure to give the product as a white solid.
ESI-MS [m/z]: 380.0 [M+H]$^+$. $^1$H-NMR (400 MHz, d$^6$-DMSO): δ=8.6 (s, 1H), 8.3 (s, 3H), 8.1 (d, 1H), 7.9 (s, 1H), 7.8 (m, 1H), 7.65 (m, 2H), 7.5 (m, 1H), 4.2 (m, 2H), 4.0 (m, 2H), 3.9 (m, 1H).

Example 45

Preparation of 5-(azetidin-3-yl)-1-(phenylsulfonyl)-1H-indazole, formic acid salt (compound 45)

a) Preparation of tert-butyl 3-(1-(phenylsulfonyl)-1H-indazol-5-yl)azetidine-1-carboxylate This compound was prepared from tert-butyl 3-(1H-indazol-5-yl)azetidine-1-carboxylate and benzenesulfonylchloride by the method outlined under 44.c).
ESI-MS [m/z]: 414.1 [M+H]$^+$.

b) Preparation of 5-(azetidin-3-yl)-1-(phenylsulfonyl)-1H-indazole, formic acid salt This compound was prepared from tert-butyl 3-(1-(phenylsulfonyl)-1H-indazol-5-yl)azetidine-1-carboxylate by the method outlined under 44.d).

ESI-MS [m/z]: 314.1 [M+H]$^+$. $^1$H-NMR (400 MHz, d$^6$-DMSO): δ=8.55 (s, 1H), 8.3 (s, 3H), 8.1 (d, 1H), 7.9 (m, 3H), 7.7 (m, 2H), 7.6 (m, 2H), 4.2 (m, 2H), 4.05 (m, 2H), 3.9 (m, 1H).

Example 46

Preparation of 5-Azetidin-3-yl-1-benzenesulfonyl-1H-pyrrolo[2,3-b]pyridine, formic acid salt (compound 46)

a) Preparation of 3-(1H-Pyrrolo[2,3-b]pyridin-5-yl)-azetidine-1-carboxylic acid tert-butyl ester In an inert atmosphere, zinc dust (223 mg, 3.41 mmol) was vigorously stirred in dimethylacetamide (1.5 ml) and heated to 65° C. Subsequently, trichloromethylsilane (50 µl, 0.38 mmol) and dibromoethane (30 µl, 0.38 mmol) were added, and the reaction mixture was stirred for further 30 minutes at 65° C. 3-Iodo-azetidine-1-carboxylic acid tert-butyl ester (462 mg, 1.89 mmol) in dimethylacetamide (2 ml) was added dropwise to the above prepared solution at 65° C. and stirred for 30 minutes. 5-Iodo-1H-pyrrolo[2,3-b]pyridine (697 mg, 2.46 mmol) in dimethylacetamide (4 ml) was added to the reaction mixture. Subsequently, [1,1-bis(diphenylphosphino)ferrocene]dichloropalladium(II)-dichlormethane (93 mg, 0.11 mmol) and copper(I)iodide (108 mg, 0.57 mmol) were added. The reaction mixture was heated to 85° C. for 5 hours, cooled to room temperature, diluted with ethyl acetate and filtered over Celite. The residue was extracted 3 times with water. The organic layer was dried over magnesium sulphate, filtered, and the solvent was evaporated under reduced pressure. The residue was purified by column chromatography on silica gel (EtOAc:cylcohexane) to afford the title compound (104 mg, 20% yield).
ESI-MS [m/z]: 274.1 [M+H]$^+$.

b) Preparation of 3-(1-Benzenesulfonyl-1H-pyrrolo[2,3-b]pyridin-5-yl)-azetidine-1-carboxylic acid tert-butyl ester 3-(1H-Pyrrolo[2,3-b]pyridin-5-yl)-azetidine-1-carboxylic acid tert-butyl ester (56 mg, 0.2 mmol) was dissolved in DMA (2 ml) and cooled to 0° C. Sodium hydride (16 mg, 0.37 mmol, 55%) was added, and the reaction mixture was stirred for 30 minutes at 0° C. Benzenesulfonyl chloride (40 µl, 0.29 mmol) was added slowly to the reaction mixture. Stirring was continued for 3 hours. Water and ethyl acetate was added to the reaction mixture. The organic phase was extract three times with water. The organic phase was dried over magnesium sulphate, filtered, and the solvent was evaporated under reduced pressure. The residue was purified by column chromatography on silica gel (ethylacetate:cylcohexane) to afford the title compound (10 mg, 12% yield).
ESI-MS [m/z]: 414.1 [M+H]$^+$.

c) Preparation of 5-Azetidin-3-yl-1-benzenesulfonyl-1H-pyrrolo[2,3-b]pyridine, formic acid salt 3-(1-Benzenesulfonyl-1H-pyrrolo[2,3-b]pyridin-5-yl)-azetidine-1-carboxylic acid tert-butyl ester (7 mg, 0.02 mmol) was dissolved in formic acid (1 ml) at 0° C. The reaction mixture was stirred at room temperature for 1 hour. Subsequently volatile compounds were evaporated under reduced pressure to give the product (5 mg, 74% yield).

ESI-MS [m/z]: 314.1 [M+H]$^+$. $^1$H-NMR (500 MHz, d$^6$-DMSO): δ=8.45 (bs, 1H), 8.45 (s, 1H), 8.2 (s, 1H), 8.1 (d, 2H), 7.9 (d, 1H), 7.7 (t, 1H), 7.6 (m, 2H), 6.85 (d, 1H), 4.2 (m, 3H), 4.1 (m, 2H).

Example 47

Preparation of 5-Azetidin-3-yl-1-(3-difluoromethoxy-benzenesulfonyl)-1H-pyrrolo[2,3-b]pyridine, hydrochloride (compound 47)

a) Preparation of 3-[1-(3-Difluoromethoxy-benzenesulfonyl)-1H-pyrrolo[2,3-b]pyridine-5-yl]-azetidine-1-carboxylic acid tert-butyl ester This compound was prepared from 3-(1H-pyrrolo[2,3-b]pyridine-5-yl)-azetidine-1-carboxylic acid tert-butyl ester and 3-Difluoromethoxy-benzenesulfonyl chloride by the method outlined under Example 46.b.
ESI-MS [m/z]: 480.1 [M+H]$^+$.

b) Preparation of 5-azetidin-3-yl-1-(3-difluoromethoxy-benzenesulfonyl)-1H-pyrrolo[2,3-b]pyridine, hydrochloride salt This compound was prepared from 3-[1-(3-difluoromethoxy-benzenesulfonyl)-1H-pyrrolo[2,3-b]pyridine-5-yl]-azetidine-1-carboxylic acid tert-butyl ester by analogy to the method outlined in example 46.c and subsequently converted into the hydrochloride salt.
ESI-MS [m/z]: 380.1 [M+H]$^+$.

Example 48

5-(Azetidin-3-yl)-3-chloro-1-(3-difluoromethoxyphenylsulfonyl)-1H-indole (compound 48) ESI-MS [m/z]: 413.1 [M+H]$^+$ Example 49

5-(Azetidin-3-yl)-1-(8-quinolinylsulfonyl)-1H-indole, trifluoroacetic acid salt (compound 49) ESI-MS [m/z]: 364.0 [M+H]$^+$ Example 50

5-(Azetidin-3-yl)-1-(4-fluoro-3-(oxazol-4-yl)phenylsulfonyl)-1H-indole, trifluoroacetic acid salt (compound 50) ESI-MS [m/z]: 398.1 [M+H]$^+$ Example 51

5-(Azetidin-3-yl)-1-[5-(2-methylthiazol-4-yl)-2-thienylsulfonyl]-1H-indole, trifluoroacetic acid salt (compound 51) ESI-MS [m/z]: 416.0 [M+H]$^+$ Example 52

5-(Azetidin-3-yl)-1-[6-(morpholin-4-yl)-pyridine-3-ylsulfonyl]-1H-indole (compound 52) ESI-MS [m/z]: 399.1 [M+H]$^+$ Example 53

5-(Azetidin-3-yl)-1-(6-quinolinylsulfonyl)-1H-indole, trifluoroacetic acid salt (compound 53) ESI-MS [m/z]: 364.1 [M+H]$^+$

Example 54

5-(Azetidin-3-yl)-1-(5-methylpyridine-2-ylsulfonyl)-1H-indole, trifluoroacetic acid salt (compound 54) ESI-MS [m/z]: 328.1 $[M+H]^+$

Example 55

5-(Azetidin-3-yl)-1-(6-chloroimidazo[2,1-b]thiazol-5-ylsulfonyl)-1H-indole, trifluoroacetic acid salt (compound 55) ESI-MS [m/z]: 393.1 $[M+H]^+$

Example 56

5-(Azetidin-3-yl)-1-(4-methyl-3,4-dihydro-2H-pyrido[3,2-b][1,4]oxazin-7-ylsulfonyl)-1H-indole, trifluoroacetic acid salt (compound 56) ESI-MS [m/z]: 385.2 $[M+H]^+$

Example 57

5-(Azetidin-3-yl)-1-[2-(morpholin-4-yl)-pyridine-3-ylsulfonyl]-1H-indole (compound 52) ESI-MS [m/z]: 399.1 $[M+H]^+$

II. Biological Investigations

Displacement of Radioligands Binding to the Following Cloned Human Receptors 1. Preparation of Membranes by Ultrasonic Treatment and Differential Centrifugation Cells from stable clonal cell lines expressing the corresponding receptor (5-HT$_6$, $_1$-adrenergic, dopamine D$_2$ or histamine H$_1$ receptors) were washed with PBS (w/o Ca$^{++}$, Mg$^{++}$) and harvested in PBS with 0.02% EDTA. The cells were collected by centrifugation at 500 g for 10 min. at 4° C., washed with PBS and centrifuged (500 g, 10 min. 4° C.). The pellets were stored at –80° C. until use. For membrane preparation, the thawed cell pellet was resuspended in ice-cold sucrose buffer (0.25 M sucrose, 10 mM Hepes (pH 7.4), 1 mM Phenylmethylsulfonyl fluoride (PMSF) in DMSO, 5 g/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1.000 g for 10 min. at 4° C. The sucrose buffer supernatant was then centrifuged at 60.000 g for 1 h at 4° C. (Beckman Ultrazentrifuge XL 80). The pellet was resuspended in 30 ml ice-cold Tris buffer (20 mM TRIS (pH 7.4), 5 g/ml Pepstatin A, 0.1 mM PMSF, 3 mM EDTA) by pipetting through a 10 ml serological pipet and centrifuged for 1 h at 4° C. at 60.000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at –80° C. or in liquid nitrogen for long-term storage.

2. Receptor Binding Experiments

All receptor binding experiments were carried out in the corresponding assay buffer in a total volume of 200 µl in the presence of various concentrations of test compound ($10^{-5}$ M to $10^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96well-plate harvester. After the plates had been dried for 2 h at 55° C. in a drying chamber scintillation cocktail (BetaPlate Scint; PerkinElmer) was added. Radioactivity was measured in a Microbeta Trilux two hours after the addition of the scintillation mixture. Data derived from liquid scintillation counting were analysed by iterative non-linear regression analysis with the use of the Statistical Analysis System (SAS): a program similar to "LIGAND" as described by Munson and Rodbard (Analytical Biochemistry 107, 220-239 (1980).

a) 5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described in section 1. For these membranes a $K_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 µM pargyline, pH 7.4) to a concentration of 8 µg protein/assay and homogenized by gentle vortexing For inhibition studies, 1 nM [$^3$H]-Lysergic Acid Diethylamide was incubated in the presence of various concentrations of test compound in assay buffer. Non-specific binding was defined with 1 µM methiothepin. The binding reaction was carried out for 3.5 h at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

a) Dopamine D$_2$ Receptor Binding Assay

HEK293 cells stably expressing the dopamine D$_2$ receptor (NCBI Reference Sequence NM_000795) were cultured in RPMI1640 medium supplemented with 25 mM HEPES, 10% fetal calf serum and 1-2 mM glutamine. The membrane preparation was performed as described in section 1. For these membranes a $K_D$ of 0.22 nM for [$^{125}$I]-iodospiperone (PerkinElmer Life Sciences, NEX284) was determined by means of saturation binding experiments. On the day of the assay, the membranes were thawed, diluted in assay buffer (50 mM Tris-HCl, 120 mM NaCl, 5 mM MgCl$_2$, 5 mM KCl, 1.5 mM CaCl$_2$, pH 7.4) to a concentration of 15 µg protein/assay and homogenized by gentle vortexing. For inhibition studies, 0.01 nM [$^{125}$I]-iodospiperone (PerkinElmer Life Sciences, NEX284) was incubated in the presence of various concentrations of test compound in assay buffer. Non-specific binding was defined with 1 µM haloperidol. The binding reaction was carried out for 1 h at room temperature and terminated by filtration on Packard Unifilter GF/B (0.1% PEI) plates, followed by 6 wash cycles with an ice-cold 7% polyethylenglycol solution.

b) $_1$-Adrenergic Receptor Binding Assay

CHO-K$_1$ cells stably expressing the $_1$-adrenergic receptor (NCBI Reference Sequence NM_033303) were cultured in RPMI1640 medium supplemented with 25 mM HEPES, 10% fetal calf serum and 1-2 mM glutamine. The membrane preparation was performed as described in section 1. For these membranes a $K_D$ of 0.12 nM for [$^3$H]-prazosine (PerkinElmer Life Sciences, NET823) was determined by means of saturation binding experiments. On the day of the assay, the membranes were thawed, diluted in assay buffer (50 mM Tris-HCl, pH 7.4) to a concentration of 4 µg protein/assay and homogenized by gentle vortexing. For inhibition studies, 0.1 nM [$^3$H]-prazosine (PerkinElmer Life Sciences, NET823) was incubated in the presence of various concentrations of test compound in assay buffer. Non-specific binding was defined with 1 μM phentolamine. The binding reaction was carried out for 1 h at room temperature and terminated by filtration on Packard Unifilter GF/C (0.1% PEI) plates, followed by 3 wash cycles with ice-cold assay buffer.

c) $H_1$ Receptor Binding Assay

CHO-$K_1$ cells stably expressing the histamine $H_1$ receptor (Euroscreen-ES-390-C, NCBI Reference Sequence NM_000861) were cultured in RPMI1640 medium supplemented with 25 mM HEPES, 10% fetal calf serum and 1-2 mM glutamine. The membrane preparation was performed as described in section 1. For these membranes a $K_D$ of 0.83 nM for [$^3$H]-pyrilamine (PerkinElmer Life Sciences, NET594) was determined by means of saturation binding experiments. On the day of the assay, the membranes were thawed, diluted in assay buffer (50 mM $Na_2HPO_4$, 50 mM $KH_2PO_4$, pH 7.4) to a concentration of 6 μg protein/assay and homogenized by gentle vortexing. For inhibition studies, 1 nM [$^3$H]-pyrilamine (PerkinElmer Life Sciences, NET594) was incubated in the presence of various concentrations of test compound in assay buffer. Non-specific binding was defined with 1 μM pyrilamine. The binding reaction was carried out for 50 minutes at room temperature and terminated by filtration on Packard Unifilter GF/C (0.3% PEI) plates, followed by 2 wash cycles with ice-cold assay buffer.

3. Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). $IC_{50}$, nH and $K_i$ values were expressed as geometrical mean. For receptors with a low affinity for the test compound, where the highest tested compound concentration inhibited less than 30% of specific radioligand binding, $K_i$ values were determined according to the equation of Cheng and Prusoff (Biochem. Pharmacol. 1973, 22, 2099-2108) and expressed as greater than (>).

The results of the receptor binding studies are expressed as receptor binding constants $K_i$(5-$HT_6$), $K_i$($D_2$), $K_i$($\alpha_1$-adrenergic) and $K_i$($H_1$), respectively, as described herein before, and given in table I.

In these tests, the compounds according to the invention exhibit very good affinities for the 5-$HT_6$ receptor ($K_i$<250 nM or <50 nM or <10 nM and frequently <5 nM). Furthermore those compounds bind selectively to the 5-$HT_6$ receptor, as compared to the affinity for the $D_2$, the $\alpha_1$-adrenergic or the $H_1$ receptors. These compounds exhibit little affinities for the $D_2$, $\alpha_1$-adrenergic or $H_1$ receptors ($K_i$>250 nM or >1000 nM and frequently >10000 nM).

TABLE I

| Example | $K_i$(5-$HT_6$) | $K_i$($D_2$) | $K_i$($\alpha_1$-adrenergic) | $K_i$($H_1$) |
|---|---|---|---|---|
| compound 2 | ++++ | --- | -- | --- |
| compound 3 | + | -- | n.d. | n.d. |
| compound 4 | ++ | -- | - | n.d. |
| compound 5 | ++++ | -- | - | -- |
| compound 6 | + | -- | n.d | n.d. |
| compound 7 | ++++ | --- | -- | -- |
| compound 8 | + | --- | n.d. | n.d. |
| compound 19 | ++++ | --- | -- | --- |
| compound 20 | ++++ | -- | -- | --- |
| compound 21 | ++++ | -- | -- | --- |
| compound 25 | ++++ | -- | - | -- |
| compound 26 | ++++ | -- | - | -- |
| compound 27 | ++++ | -- | - | -- |

TABLE I-continued

| Example | $K_i$(5-$HT_6$) | $K_i$($D_2$) | $K_i$($\alpha_1$-adrenergic) | $K_i$($H_1$) |
|---|---|---|---|---|
| compound 28 | +++ | -- | n.d. | n.d. |
| compound 29 | +++ | -- | n.d. | n.d. |
| compound 23 | ++++ | --- | -- | -- |
| compound 24 | +++ | --- | n.d. | n.d. |
| compound 30 | ++++ | -- | -- | -- |
| compound 46 | +++ | --- | --- | --- |

In table I "n.d." means not determined; "++++" $\hat{=}$ $K_i$ < 5 nM; "+++" $\hat{=}$ $K_i$ < 10 nM; "++" $\hat{=}$ $K_i$ < 50 nM; "+" $\hat{=}$ $K_i$ < 250 nM; "–" $\hat{=}$ $K_i$ > 250 nM; "--" $\hat{=}$ $K_i$ > 1000; "---" $\hat{=}$ $K_i$ > 10000 nM.

We claim:
1. Compounds of formula (I)

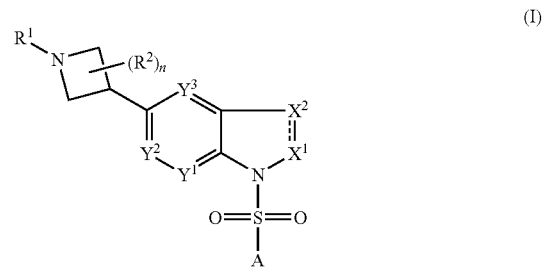

wherein

A is $C_1$-$C_6$-alkyl, $C_1$-$C_6$-haloalkyl, $C_1$-$C_6$-hydroxyalkyl, $C_2$-$C_6$-alkenyl, $C_2$-$C_6$-haloalkenyl, $C_3$-$C_6$-cycloalkyl, aryl-$C_1$-$C_4$-alkyl, aryl-$C_2$-$C_4$-alkenyl, aryl or hetaryl wherein cycloalkyl and the aryl or hetaryl moieties in the 5 last mentioned radicals may be unsubstituted or may carry 1, 2 or 3 substituents $R^a$, wherein $R^a$ is selected from the group consisting of halogen, CN, $NO_2$, $C_1$-$C_6$-alkyl, $C_1$-$C_6$-haloalkyl, $C_1$-$C_6$-hydroxyalkyl, $C_1$-$C_6$-alkoxy-$C_1$-$C_4$-alkyl, $C_2$-$C_6$-alkenyl, $C_2$-$C_6$-haloalkenyl, $C_3$-$C_6$-cycloalkyl, $C_3$-$C_6$-halocycloalkyl, $C_1$-$C_6$-alkoxy, $C_1$-$C_6$-hydroxyalkoxy, $C_1$-$C_6$-alkoxy-$C_1$-$C_4$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_6$-alkylcarbonyl, $C_1$-$C_6$-haloalkyl-carbonyl, $C_1$-$C_6$-alkylcarbonylamino, $C_1$-$C_6$-haloalkylcarbonylamino, carboxy, NH—C(O)—$NR^3R^4$, $NR^3R^4$, $NR^3R^4$—$C_1$-$C_6$-alkylene, O—$NR^3R^4$, wherein $R^3$ and $R^4$ in the last 4 mentioned radicals are independently of each other hydrogen, $C_1$-$C_6$-alkyl, $C_1$-$C_6$-haloalkyl, $C_1$-$C_6$-alkoxy or together with the nitrogen atom form an N-bound 5- to 7-membered saturated heterocycle, which may contain a further heteroatom selected from O, S and N as ring member, a saturated or unsaturated 3- to 7-membered heterocyclic ring, phenyl, benzyl, phenylsulfonyl, phenoxy and benzyloxy, wherein the 3- to 7-membered heterocyclic ring comprises as ring members 1, 2, 3 or 4 heteroatoms selected from N, O and S and may carry 1, 2 or 3 substituents selected from the group consisting of hydroxy, halogen, $C_1$-$C_6$-alkyl, $C_1$-$C_6$-haloalkyl and $C_1$-$C_6$-alkoxy and wherein the phenyl radical in phenyl, benzyl, phenylsulfonyl, phenoxy or benzyloxy is unsubstituted or may carry 1, 2 or 3 substituents selected from the group consisting of halogen, CN, $NO_2$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkylcarbonylamino, $C_1$-$C_6$-haloalkylcarbonylamino, carboxy, NH—C(O)—$NR^5R^6$, $NR^5R^6$, $NR^5R^6$—$C_1$-$C_6$-alkylene, O—$NR^5R^6$, wherein $R^5$ and $R^6$ are independently of each other hydrogen, $C_1$-$C_6$-alkyl, $C_1$-$C_6$-haloalkyl, $C_1$-$C_6$-alkoxy and together with the nitrogen atom form an N-bound 5- to 7-membered saturated heterocycle, which may contain a further heteroatom selected from O, S and N as ring member;

----- is a single bond or a double bond;

$X^1$ and $X^2$ are independently from each other N or $CR^{x1}$, if ----- is a double bond, or $NR^{x2}$ or $CR^{x3}R^{x4}$, if ----- is a single bond, wherein $R^{x1}$, $R^{x3}$ and $R^{x4}$ are selected from the group consisting of hydrogen, halogen, CN, $NO_2$, $C_1$-$C_6$-alkyl, $C_1$-$C_6$-alkoxy, $C_1$-$C_6$-alkylcarbonyl, $C_1$-$C_6$-haloalkyl, $C_1$-$C_6$-haloalkoxy, $C_1$-$C_6$-haloalkylcarbonyl, $C_1$-$C_6$-hydroxyalkyl, $C_3$-$C_6$-cycloalkyl, phenyl, phenoxy and benzyloxy, wherein the last four mentioned radicals may be unsubstituted or may carry 1, 2 or 3 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy, or two geminal radicals $R^{x3}$ and $R^{x4}$ together with the carbon atom to which they are bound may form a carbonyl group or a 3- to 6-membered carbocyclic or heterocyclic spiro-annulated ring, which may be unsubstituted or may carry 1, 2, 3, 4 or 5 substituents selected from halogen, CN, $NO_2$, $C_1$-$C_4$-alkyl, $C_1$-$C_4$-fluoroalkyl, $C_1$-$C_4$-alkoxy or $C_1$-$C_4$-fluoroalkoxy, and $R^{x2}$ is hydrogen, $C_1$-$C_6$-alkyl, $C_1$-$C_6$-alkylcarbonyl, $C_1$-$C_6$-haloalkyl, $C_1$-$C_6$-haloalkylcarbonyl, $C_1$-$C_6$-hydroxyalkyl, $C_3$-$C_6$-cycloalkyl or phenyl, wherein the last two mentioned radicals may be unsubstituted or may carry 1, 2 or 3 substituents selected from halogen, CN, $NO_2$, $C_1$-$C_4$-fluoroalkyl, $C_1$-$C_4$-alkoxy or $C_1$-$C_4$-fluoroalkoxy;

or two vicinal radicals selected from $R^{x1}$, $R^{x2}$, $R^{x3}$ or $R^{x4}$ together with $X^1$ and $X^2$ form a five- or six-membered carbocyclic or heterocyclic fused ring, which may be unsubstituted or may carry 1, 2, 3 or 4 substituents selected from halogen, CN, $NO_2$, $C_1$-$C_4$-fluoroalkyl, $C_1$-$C_4$-alkoxy or $C_1$-$C_4$-fluoroalkoxy;

$Y^1$, $Y^2$ and $Y^3$ are independently from each other N or $CR^y$, wherein $R^y$ is hydrogen, halogen, CN, $NO_2$, $C_1$-$C_6$-alkoxy, $C_1$-$C_6$-alkylcarbonyl, $C_1$-$C_6$-haloalkyl, $C_1$-$C_6$-haloalkoxy, $C_1$-$C_6$-halo-alkylcarbonyl, $C_1$-$C_6$-hydroxyalkyl, $C_3$-$C_6$-cycloalkyl, phenyl, phenoxy or benzyloxy wherein the last four mentioned radicals may be unsubstituted or may carry 1, 2 or 3 substituents selected from halogen, CN, $NO_2$, $C_1$-$C_4$-fluoroalkyl, $C_1$-$C_4$-alkoxy or $C_1$-$C_4$-fluoroalkoxy;

wherein a maximum of 3 of the moieties $X^1$, $X^2$, $Y^1$, $Y^2$ and $Y^3$ are $NR^{x1}$ or N;

and wherein $R^1$ is hydrogen, $C_1$-$C_6$-alkyl, $C_1$-$C_6$-hydroxyalkyl, $C_1$-$C_6$-haloalkyl, $C_1$-$C_6$-alkoxy-$C_1$-$C_4$-alkyl, $C_1$-$C_6$-haloalkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, aryl $C_1$-$C_4$-alkyl, hetaryl-$C_1$-$C_4$-alkyl, $C_3$-$C_6$-alkenyl, $C_3$-$C_6$-haloalkenyl, formyl, $C_1$-$C_4$-alkylcarbonyl or $C_1$-$C_4$-alkoxycarbonyl;

$R^2$ is $C_1$-$C_4$-alkyl or $C_1$-$C_4$-haloalkyl;

n is 0, 1 or 2;

and physiologically tolerated acid addition salts and the N-oxides thereof.

2. The compounds of claim 1, wherein A is mono- or bicyclic aryl or mono- or bicyclic hetaryl, wherein the cyclic radical A is unsubstituted or may carry 1, 2 or 3 substituents $R^a$.

3. The compounds of claim 2, wherein A is phenyl, naphthyl, thienyl, pyridyl, pyrimidyl, imidazolyl, isoxazolyl, thiazolyl, triazolyl, thiadiazolyl, quinolinyl, isoquinolinyl, tetrahydroisoquinolinyl, benzofuranyl, benzothiophenyl, benzoxazinyl, benzothiazolyl, benzoxadiazolyl, benzothiadiazolyl, benzomorpholinyl, imidazo[2,1-b]thiazolyl, pyrido[3,2-b][1,4]oxazinyl, 3,4-dihydropyrido[3,2-b][1,4]oxazinyl or indanyl, wherein the cyclic radical A is unsubstituted or may carry 1, 2 or 3 substituents $R^a$.

4. The compounds of claim 3, wherein A is phenyl, which is unsubstituted or may carry 1, 2 or 3 substituents $R^a$.

5. The compounds of claim 4, wherein A is phenyl, which is unsubstituted or may carry 1, 2 or 3 substituents $R^a$, wherein the substituents $R^a$ are attached to the phenyl ring in ortho- and/or meta-position relative to the bonding-position.

6. The compounds of claim 1, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from the group consisting of halogen, CN, $NO_2$, $C_1$-$C_4$-alkyl, $C_1$-$C_4$-haloalkyl, $C_1$-$C_4$-alkoxy, and $C_1$-$C_4$-haloalkoxy.

7. The compounds of claim 6, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

8. The compounds of claim 2, wherein A is selected from the group consisting of phenyl, 2-fluorophenyl, 3-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 2-tolyl, 3-tolyl, 2-isopropylphenyl, 3-isopropylphenyl, 2-difluoromethylphenyl, 3-difluoromethylphenyl, 2-trifluoromethylphenyl, 3-trifluoromethylphenyl, biphenyl-2-yl, biphenyl-3-yl, 2-methoxyphenyl, 3-methoxyphenyl, 2-difluoro-methoxyphenyl, 3-difluoromethoxyphenyl, 2-trifluoromethoxyphenyl, 3-trifluoro-methoxyphenyl, 2-phenoxyphenyl, 3-phenoxyphenyl, 4-(oxazol-5-yl)phenyl, 3-(pyrrolidin-1-yl)phenyl, 1-naphtyl, 2-naphtyl, pyridin-2-yl, pyridin-3-yl, pyridin-4-yl, 2-(pyrrolidin-1-yl)pyridin-4-yl, 6-morpholin-4-ylpyridin-3-yl, 6-phenoxypyridin-3-yl, thien-2-yl, 5-methylthien-2-yl, 5-(pyridin-2-yl)thien-2-yl, 5-(2-methylthiazol-4-yl)-thien-2-yl, 5-chloro-3-methyl-benzo[b]thien-2-yl, 2-methylthiazol-5-yl, 2,4-dimethyl-thiazol-5-yl, 4-methylthiazol-2-yl, 5-methylthiazol-2-yl, 3,5-dimethylisoxazol-4-yl, 1-methylimidazol-4-yl, benzothiazol-7-yl, 4-methylbenzomorpholin-8-yl, quinolin-8-yl, 5-methylpyridin-2-yl, 2-morpholin-4-ylpyridin-3-yl, 4-fluoro-3-(oxazol-4-yl)phenyl, quinolin-6-yl, 6-chloroimidazo[2,1-b]thiazol-5-yl, 4-methyl-3,4-dihydropyrido[3,2-b][1,4]oxazin-7-yl, and isoquinolin-4-yl, 2,1,3-benzoxdiazol-4-yl.

9. The compounds of claim 1, wherein $R^{x1}$, $R^{x3}$ and $R^{x4}$ are selected from the group consisting of hydrogen, halogen, CN, $NO_2$, $C_1$-$C_4$-alkyl, $C_1$-$C_4$-alkoxy, $C_1$-$C_4$-haloalkyl and $C_1$-$C_4$-haloalkoxy.

10. The compounds of claim 9, wherein $R^{x1}$, $R^{x3}$ and $R^{x4}$ are selected from the group consisting of hydrogen, halogen and CN.

11. The compounds of claim 10, wherein $R^{x1}$, $R^{x3}$ and $R^{x4}$ are hydrogen.

12. The compounds of claim 1, wherein $R^{x2}$ is hydrogen or $C_1$-$C_4$-alkyl.

13. The compounds of claim 1, wherein $R^y$ is hydrogen, halogen, CN, $NO_2$, $C_1$-$C_4$-alkyl, $C_1$-$C_4$-alkoxy, $C_1$-$C_4$-haloalkyl or $C_1$-$C_4$-haloalkoxy.

14. The compounds of claim 13, wherein $R^y$ is hydrogen or halogen.

15. The compounds of claim 1, wherein $R^1$ is hydrogen, $C_1$-$C_4$-alkyl, $C_1$-$C_4$-haloalkyl or $C_3$-$C_6$-cycloalkyl.

16. The compounds of claim 15, wherein $R^1$ is hydrogen.

17. The compounds of claim 1, wherein n is 0.

18. The compounds of claim 1, wherein ---- is a single bond.

19. The compounds of claim 1, selected from compounds of formulae I.A.1 to I.A.6, wherein the radicals A, $R^1$, $R^2$, n and $R^{x2}$ have the meanings given in claim 1, $R^{x3}$ and $R^{x3'}$ independently from each other have the meanings given for $R^{x3}$ in claim 1, $R^{x4}$ and $R^{x4'}$ independently from each other have the meanings given for $R^{x4}$ in claim 1 and $R^y$, $R^{y'}$ and $R^{y''}$ independently from each other have the meaning given for $R^y$ in claim 1.

20. The compounds of formula I.A.1 of claim 19.

21. The compounds of claim 19, wherein A is phenyl, which is unsubstituted or may carry 1, 2 or 3 substituents W.

22. The compounds of claim 21, wherein A is phenyl, which is unsubstituted or may carry 1, 2 or 3 substituents $R^a$, wherein the substituents $R^a$ are attached to the phenyl ring in ortho- and/or meta-position relative to the bonding-position.

23. The compounds of claim 19, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from the group consisting of halogen, CN, $NO_2$, $C_1$-$C_4$-alkyl, $C_1$-$C_4$-haloalkyl, $C_1$-$C_4$-alkoxy, and $C_1$-$C_4$-haloalkoxy.

24. The compounds of claim 19, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

25. The compounds of claim 19, wherein $R^y$, $R^{y'}$ and $R^{y''}$ are hydrogen.

26. The compounds of claim 19, wherein $R^{x2}$, $R^{x3}$, $R^{x4}$, $R^{x3'}$ and $R^{x4'}$ are hydrogen.

27. The compounds of claim 19, wherein $R^1$ is hydrogen, $C_1$-$C_4$-alkyl, $C_1$-$C_4$-haloalkyl or $C_3$-$C_6$-cycloalkyl.

28. The compounds of claim 27, wherein $R^1$ is hydrogen.

29. The compounds of claim 19, wherein n is 0.

30. The compounds of claim 1, wherein ---- is a double bond.

31. The compounds of claim 1, selected from compounds of formulae I.B.1 to I.B.8

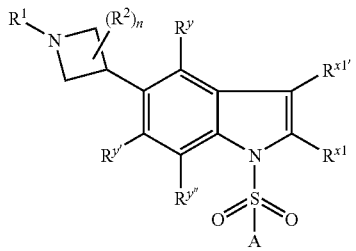
(I.B.1)

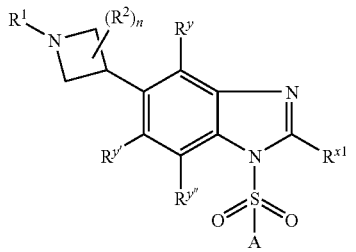
(I.B.2)

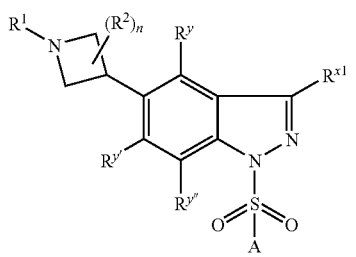
(I.B.3)

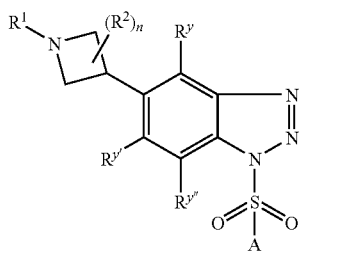
(I.B.4)

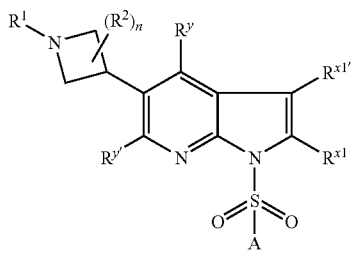
(I.B.5)

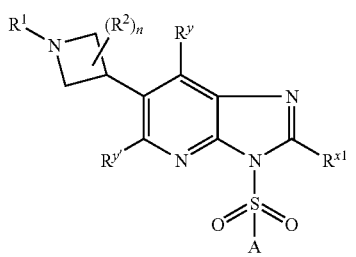
(I.B.6)

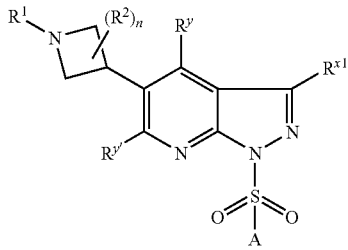
(I.B.7)

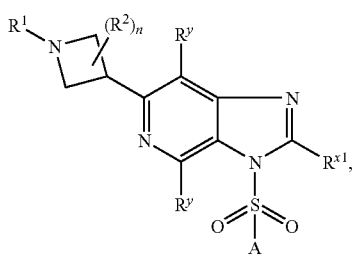
(I.B.8)

wherein the radicals A, $R^1$, $R^2$ and n have the meanings given in claim 1, $R^{x1}$ and $R^{x1'}$ independently from each other have the meaning given for $R^{x1}$ in claim 1 and $R^y$, $R^{y'}$ and $R^{y''}$ independently from each other have the meaning given for $R^y$ in claim 1.

32. The compounds of formula I.B.1 of claim 31.

33. The compounds of claim 31, wherein A is phenyl, which is unsubstituted or may carry 1, 2 or 3 substituents W.

34. The compounds of claim 33, wherein A is phenyl, which is unsubstituted or may carry 1, 2 or 3 substituents $R^a$ wherein the substituents $R^a$ are attached to the phenyl ring in ortho- and/or meta-position relative to the bonding-position.

35. The compounds of claim 31, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, oxazolyl, phenyl and phenoxy, wherein the phenyl radical in the 2 last-mentioned radicals is unsubstituted or may carry 1, 2 or 3 substituents selected from the group consisting of halogen, CN, $NO_2$, $C_1$-$C_4$-alkyl, $C_1$-$C_4$-haloalkyl, $C_1$-$C_4$-alkoxy, and $C_1$-$C_4$-haloalkoxy.

36. The compounds of claim 31, wherein A carries 1, 2 or 3 radicals $R^a$ which are selected from the group consisting of halogen, CN, $C_1$-$C_4$-alkyl, $C_1$-$C_4$-haloalkyl, $C_1$-$C_4$-alkoxy, $C_1$-$C_4$-haloalkoxy and $C_3$-$C_6$-cycloalkyl.

37. The compounds of claim 31, wherein $R^y$, $R^{y'}$ and $R^{y''}$ are hydrogen.

38. The compounds of claim 31, wherein $R^{x1}$ is hydrogen and $R^{x1'}$ is hydrogen or halogen.

39. The compounds of claim 31, wherein $R^1$ is hydrogen, $C_1$-$C_4$-alkyl, $C_1$-$C_4$-haloalkyl or $C_3$-$C_6$-cycloalkyl.

40. The compounds of claim 39, wherein $R^1$ is hydrogen.

41. The compounds of claim 31, wherein n is 0.

42. The compounds of claim 1, which are selected from the group consisting of
5-azetidin-3-yl-1-(4-difluoromethoxybenzenesulfonyl)-1H-indole,
5-azetidin-3-yl-1-benzenesulfonyl-1H-indole,
5-azetidin-3-yl-1-(4-oxazol-5-yl-benzenesulfonyl)-1H-indole,
1-(4-Difluoromethoxy-benzenesulfonyl)-5-(1-propyl-azetidin-3-yl)-1H-indole,
1-benzenesulfonyl-5-(1-propylazetidin-3-yl)-1H-indole, 1-(4-oxazol-5-yl-benzenesulfonyl)-5-(1-propylazetidin-3-yl)-1H-indole,
5-azetidin-3-yl-1-benzenesulfonyl-2,3-dihydro-1H-indole,
5-azetidin-3-yl-1-(4-oxazol-5-yl-benzenesulfonyl)-2,3-dihydro-1H-indole,
1-Benzenesulfonyl-5-(1-propyl-azetidin-3-yl)-2,3-dihydro-1H-indole,
1-(4-oxazol-5-yl-benzenesulfonyl)-5-(1-propyl-azetidin-3-yl)-2,3-dihydro-1H-indole,
3-[1-(4-isopropyl-benzenesulfonyl)-1H-indol-5-yl]-azetidine-1-carboxylic acid tert-butyl ester,
3-[1-(4-Oxazol-5-ylbenzenesulfonyl)-1H-indol-5-yl]-azetidine-1-carboxylic acid tert-butyl ester,
3-[1-(3-Trifluoromethylbenzenesulfonyl)-1H-indol-5-yl]-azetidine-1-carboxylic acid tert-butyl ester,
3-[1-(3-Trifluoromethoxybenzenesulfonyl)-1H-indol-5-yl]-azetidine-1-carboxylic acid tert-butyl ester,
3-[1-(3-Difluoromethoxybenzenesulfonyl)-1H-indol-5-yl]-azetidine-1-carboxylic acid tert-butyl ester,
3-[1-(2-Trifluoromethylbenzenesulfonyl)-1H-indol-5-yl]-azetidine-1-carboxylic acid tert-butyl ester,
3-[1-(2-Trifluoromethoxybenzenesulfonyl)-1H-indol-5-yl]-azetidine-1-carboxylic acid tert-butyl ester,
3-[1-(Pyridine-3-sulfonyl)-1H-indol-5-yl]-azetidine-1-carboxylic acid tert-butyl ester,
5-azetidin-3-yl-1-(3-trifluoromethyl-benzenesulfonyl)-1H-indole,
5-Azetidin-3-yl-1-(3-trifluoromethoxybenzenesulfonyl)-1H-indole,
5-Azetidin-3-yl-1-(3-difluoromethoxybenzenesulfonyl)-1H-indole,
5-Azetidin-3-yl-1-(2-trifluoromethylbenzenesulfonyl)-1H-indole,
5-Azetidin-3-yl-1-(2-trifluoromethoxybenzenesulfonyl)-1H-indole,
Azetidin-3-yl-1-(pyridine-3-sulfonyl)-1H-indole,
5-(1-propyl-azetidin-3-yl)-1-(3-trifluoromethylbenzenesulfonyl)-1H-indole,
5-(1-Propylazetidin-3-yl)-1-(3-trifluoromethoxybenzenesulfonyl)-1H-indole,
5-(1-Propylazetidin-3-yl)-1-(3-difluoromethoxybenzenesulfonyl)-1H-indole,
5-(1-Ethylazetidin-3-yl)-1-benzenesulfonyl-1H-indole,
5-(1-Methylazetidin-3-yl)-1-benzenesulfonyl-1H-indole,
5-Azetidin-3-yl-1-(3-trifluoromethyl-benzenesulfonyl)-2,3-dihydro-1H-indole,
5-Azetidin-3-yl-1-benzenesulfonyl-3-chloro-1H-indole,
4-(5-(5-(azetidin-3-yl)-1H-indazol-1-ylsulfonyl)-2-fluorophenyl)oxazole,
5-(Azetidin-3-yl)-1-(naphthalene-2-sulfonyl)-1H-indole,
5-(Azetidin-3-yl)-1-(2-fluoro-benzenesulfonyl)-1H-indole,
5-(Azetidin-3-yl)-1-(3-phenoxy-benzenesulfonyl)-1H-indole,
5-(Azetidin-3-yl)-1-(3-chloro-benzenesulfonyl)-1H-indole,
5-(Azetidin-3-yl)-1-(3-fluoro-benzenesulfonyl)-1H-indole,
5-(Azetidin-3-yl)-1-(3-trifluoromethyl-benzenesulfonyl)-2,3-dihydro-1H-indole,
5-(Azetidin-3-yl)-1-(4-fluoro-benzenesulfonyl)-1H-indole,
5-(Azetidin-3-yl)-1-(1-biphenyl-2-sulfonyl)-1H-indole,
5-(Azetidin-3-yl)-1-(naphthalene-1-sulfonyl)-1H-indole,
5-(Azetidin-3-yl)-1-(3-trifluoromethoxy-benzenesulfonyl)-2,3-dihydro-1H-indole,
5-(Azetidin-3-yl)-1-(3-difluoromethoxy-benzenesulfonyl)-2,3-dihydro-1H-indole,
5-(azetidin-3-yl)-1-(3-(difluoromethoxy)phenylsulfonyl)-1H-indazole,
5-(azetidin-3-yl)-1-(phenylsulfonyl)-1H-indazole,
5-Azetidin-3-yl-1-benzenesulfonyl-1H-pyrrolo[2,3-b]pyridine,
5-Azetidin-3-yl-1-(3-difluoromethoxybenzenesulfonyl)-1H-pyrrolo[2,3-b]pyridine,
5-(Azetidin-3-yl)-3-chloro-1-(3-difluoromethoxyphenylsulfonyl)-1H-indole,
5-(Azetidin-3-yl)-1-(8-quinolinylsulfonyl)-1H-indole,
5-(Azetidin-3-yl)-1-(4-fluoro-3-(oxazol-4-yl)phenylsulfonyl)-1H-indole,
5-(Azetidin-3-yl)-1-[5-(2-methylthiazol-4-yl)-2-thienylsulfonyl]-1H-indole,
5-(Azetidin-3-yl)-1-[6-(morpholin-4-yl)-pyridine-3-ylsulfonyl]-1H-indole,
5-(Azetidin-3-yl)-1-(6-quinolinylsulfonyl)-1H-indole,
5-(Azetidin-3-yl)-1-(5-methylpyridine-2-ylsulfonyl)-1H-indole,
5-(Azetidin-3-yl)-1-(6-chloroimidazo[2,1-b]thiazol-5-ylsulfonyl)-1H-indole,
5-(Azetidin-3-yl)-1-(4-methyl-3,4-dihydro-2H-pyrido[3,2-b][1,4]oxazin-7-ylsulfonyl)-1H-indole,
5-(Azetidin-3-yl)-1-[2-(morpholin-4-yl)-pyridine-3-ylsulfonyl]-1H-indole, and physiologically tolerated acid addition salts and the N-oxides thereof.

43. A pharmaceutical composition comprising at least one compound of claim 1, optionally together with at least one physiologically acceptable carrier or auxiliary substance.

44. A method for suppressing the symptoms of a medical disorder selected from the group consisting of obesity, cognitive dysfunctions associated with schizophrenia, and addiction diseases, said method comprising administering an effective amount of at least one compound of claim 1 to a subject in need thereof.

* * * * *